US007309584B2

(12) United States Patent
Ruth et al.

(10) Patent No.: US 7,309,584 B2
(45) Date of Patent: Dec. 18, 2007

(54) MUTATIONS OF THE MDR1 P-GLYCOPROTEIN THAT IMPROVES ITS ABILITY TO CONFER RESISTANCE TO CHEMOTHERAPEUTIC DRUGS

(75) Inventors: Adam Ruth, Chicago, IL (US); Igor Roninson, Cohoes, NY (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 387 days.

(21) Appl. No.: 10/343,657

(22) PCT Filed: Aug. 1, 2001

(86) PCT No.: PCT/US01/24560

§ 371 (c)(1),
(2), (4) Date: Oct. 17, 2003

(87) PCT Pub. No.: WO02/10205

PCT Pub. Date: Feb. 7, 2002

(65) Prior Publication Data

US 2004/0086882 A1   May 6, 2004

Related U.S. Application Data

(60) Provisional application No. 60/222,313, filed on Aug. 1, 2000.

(51) Int. Cl.
C12P 21/06 (2006.01)
(52) U.S. Cl. ............... 435/69.1; 435/6; 435/320.1; 530/350; 536/23.5
(58) Field of Classification Search .............. None
See application file for complete search history.

(56) References Cited

U.S. PATENT DOCUMENTS 5,830,697 A * 11/1998 Sikic et al. .............. 435/69.1

OTHER PUBLICATIONS

Currier Stephen et al, Identification of residues in the first cytoplasmic loop of P-glycoprotein involved in the function of chimeric human MDR1-MDR2 transporters. Journ. of Biol. Chem. 267(35)25153-25159 (1992).

Roninson et al., Isolation of Altered-Function Mutants and Genetic Suppressor Elements of Multidrug Transporter P-Glycoprotein by Expression Selection from Retroviral Libraries. Methods in Enzymology 292:225-48 (1998).

Safa et al., "Molecular Basis of Preferential Resistance to Colchicine in Multidrug-Resistant Human Cell Conferred by GLY-185-Val-185 Substitution in P Glycoprotein" Proceeding of the National Academy of Sciences of USA 87(18) 7225-9 (Sep. 1990).

Ruth Adam et al., "Coordinate changes in drug resistance and drug-induced conformational transitions in altered-fuction mutants of the multidrug transporter P-glycoprotein" Biochem. 40(14)4332-9 (Apr. 10, 2001).

Loo et al., "Mutations to Amino Acids Located in Predicted Transmembrane Segment 6 (TM6) Modulate the Activity and Substrate Specificity of Human P-Glycoprotein," Biochemistry 33(47)14049-57 (Nov. 1994).

Loo et al., Functional consequences of glycine mutations in the predicted cytoplasmic loops of P-glycoprotein Journ of Biol. Chem. 269(10) 7243-48 (Mar. 11, 1994).

Taguchi et al., "Alteration of substrate specifically by mutations at the His-61 position in predicted transmembrane domain 1 of human MDRI/P-glycoprotein" Biochemistry 36(29)8883-9 (1997).

Choi et al., "An Altered Pattern of Cross-Resistance in Multidrug-Resistant Human cells Results from Spontaneous Mutations in the mdr1 (P-Glycoprotein) Gene" Cell 53:519-29 (May 20, 1998).

Chen et al., "Internal Duplication and Homology with Bacterial Transport Proteins in the Mdr1 (P-Glycoprotein) Gene from Multidrug-Resistant Human Cells" Cell 47:381-89 (Nov. 7, 1986).

* cited by examiner

Primary Examiner—Robert Landsman
Assistant Examiner—Gyan Chandra
(74) Attorney, Agent, or Firm—McDonnell Boehnen Hulbert & Berghoff

(57) ABSTRACT

The present invention provides mutant P-glycoprotein polypeptides that confer increased resistance to certain chemotherapeutic drugs relative to wild-type P-glycoprotein or P-glycoprotein having a glycine to valine substitution at position 185, and nucleic acid molecules encoding the same. The invention also provides antibodies that specifically bind mutant P-glycoproteins. The invention further provides methods for the diagnosis and treatment of conditions associated with P-glycoprotein-mediated multidrug resistance.

49 Claims, 12 Drawing Sheets

FIG. 3A

```
wt P-gp    1  MDLEGDRNGGAKKKNFFKLNNKSEKDKKEKKPTVSVFSMFRYSNWLDKLY  50
G185V      1  MDLEGDRNGGAKKKNFFKLNNKSEKDKKEKKPTVSVFSMFRYSNWLDKLY  50
I186N      1  MDLEGDRNGGAKKKNFFKLNNKSEKDKKEKKPTVSVFSMFRYSNWLDKLY  50
8-A4       1  MDLEGDRNGGAKKKNFFKLNNKSEKDKKEKKPTVSVFSMFRYSNWLDKLY  50
5-C3       1  MDLEGDRNGGAKKKNFFKLNNKSEKDKKEKKPTVSVFSMFRYSNWLDKLY  50
2-B2       1  MDLEGDRNGGAKKKNFFKLNNKSEKDKKEKKPTVSVFSMFRYSNWLDKLY  50
2-B1       1  MDLEGDRNGGAKKKNFFKLNNKSEKDKKEKKPTVSVFSMFRYSNWLDKLY  50
6-C1       1  MDLEGDRNGGAKKKNFFKLNNKSEKDKKEKKPTVSVFSMFRYSNWLDKLY  50
8-B4       1  MDLEGDRNGGAKKKNFFKLNNKSEKDKKEKKPTVSVFSMFRYSNWLDKLY  50
EK5        1  MDLEGDRNGGAKKKNFFKLNNKSEKDKKEKKPTVSVFSMFRYSNWLDKLY  50 wt P-gp   51  MVVGTLAAIIHGAGLPLMMLVFGEMTDIFANAGNLEDLMSNITNRSDIND  100
G185V     51  MVVGTLAAIIHGAGLPLMMLVFGEMTDIFANAGNLEDLMSNITNRSDIND  100
I186N     51  MVVGTLAAIIHGAGLPLMMLVFGEMTDIFANAGNLEDLMSNITNRSDIND  100
8-A4      51  MVVGTFAAIIHGAGLPLMMLVFGEMTDIFANAGNLEDLMSNITNRSDIND  100
5-C3      51  MVVGTLAAIIHGAGLPLMMLVFGEMTDIFANAGNLEDLMSNITNRSDIND  100
2-B2      51  MVVGTLAAIIHGAGLPLMMLVFGEMTDIFANAGNLEDLMSNITNRSDIND  100
2-B1      51  MVVGTLAAIIHGAGLPLMMLVFGEMTDIFANAGNLEDLMSNITNRSDIND  100
6-C1      51  MVVGTLAAIIHGAGLPLMMLVFGEMTDIFANAGNLEDLMSNITNRSDIND  100
8-B4      51  MVVGTLAAIIHGAGLPLMMLVFGEMTDIFANAGNLEDLMSNITNRSDIND  100
EK5       51  MVVGTLAAIIHGAGLPLMMLVFGEMTDIFANAGNLEDLMSNITNRSDIND  100 wt P-gp  101  TGFFMNLEEDMTRYAYYYSGIGAGVLVAAYIQVSFWCLAAGRQIHKIRKQ  150
G185V    101  TGFFMNLEEDMTRYAYYYSGIGAGVLVAAYIQVSFWCLAAGRQIHKIRKQ  150
I186N    101  TGFFMNLEEDMTRYAYYYSGIGAGVLVAAYIQVSFWCLAAGRQIHKIRKQ  150
8-A4     101  TGFFMNLEEDMTRYAYYYSGIGAGVLVAAYIQVSFWCLAAGRQIHKIRKQ  150
5-C3     101  TGFFMNLEEDMTRYAYYYSGIGAGVLVAAYIQVSFWCLAAGRQIHKIRKQ  150
2-B2     101  TGFFMNLEEDMTRYAYYYSGIGAGVLVAAYIQVSFWCLAAGRQIHKIRKQ  150
2-B1     101  TGFFMNLEEDMTRYAYYYSGIGAGVLVAAYIQVSFWCLAAGRQIHKIRKQ  150
6-C1     101  TGFFMNLEEDMTRYAYYYSGIGAGVLVAAYIQVSFWCLAAGRQIHKIRKQ  150
8-B4     101  TGFFMNLEEDMTRYAYYYSGIGAGVLVAAYIQVSFWCLAAGRQIHKIRKQ  150
EK5      101  TGFFMNLEEDMTRYAYYYSGIGAGVLVAAYIQVSFWCLAAGRQIHKIRKQ  150 wt P-gp  151  FFHAIMRQEIGWFDVHDVGELNTRLTDDVSKINEGIGDKIGMFFQSMATF  200
G185V    151  FFHAIMRQEIGWFDVHDVGELNTRLTDDVSKINEVIGDKIGMFFQSMATF  200
I186N    151  FFHAIMRQEIGWFDVHDVGELNTRLTDDVSKINEGNGDKIGMFFQSMATF  200
8-A4     151  FFHAIMRQEIGWFDVHDVGELNTRLTDDVSKINEGIGDKIGMFFQSMATF  200
5-C3     151  FFHAIMRQEIGWFDVHDVGELNTRLTDDVSKINEGIGDKFGMFFQSFATF  200
2-B2     151  FFHAIMRQEIGWFDVHDVGELNTRLTDDVSKINEGIGDKIGMFFQSMATF  200
2-B1     151  FFHAIMRQEIGWFDVHDVGELNTRLTDDVSKINEGIGDKIGMFFQSMATF  200
6-C1     151  FFHAIMRQEIGWFDVHDVGELNTRLTDDVSKINEGIGDKIGMFFQSMATF  200
8-B4     151  FFHAIMRQEIGWFDVHDVGELNTRLTDDVSKINEGIGDKIGMFFQSMATF  200
EK5      151  FFHAIMRQEIGWFDVHDVGELNTRLTDDVSKINEGIGDKIGMFFQSMATF  200
```

FIG. 3B

```
wt P-gp  201 FTGFIVGFTRGWKLTLVILAISPVLGLSAAVWAKILSSFTDKELLAYAKA 250
G185V    201 FTGFIVGFTRGWKLTLVILAISPVLGLSAAVWAKILSSFTDKELLAYAKA 250
I186N    201 FTGFIVGFTRGWKLTLVILAISPVLGLSAAVWAKILSSFTDKELLAYAKA 250
8-A4     201 FTGFIVGFTRGWKLTLVILAISPVLGLSAAVWAKILSSFTDKELLAYAKA 250
5-C3     201 FTGFIVGFTRGWKLTLVILAISPVLGLSAAVWAKILSSFTDKELLAYAKA 250
2-B2     201 FTGFIVGFTRGWKLTLVILAISPVLGLSAAVWAKILSSFTDKELLAYAKA 250
2-B1     201 FTGFIVGFTRGWKLTLVILAISPVLGLSAAVWAKILSSFTDKELLAYAKA 250
6-C1     201 FTGFIVGFTRGWKLTLVILAISPVLGLSAAVWAKILSSFTDKELLAYAKA 250
8-B4     201 FTGFIVGFTRGWKLTLVILAISPVLGLSAAVWAKILSSFTDKELLAYAKA 250
EK5      201 FTGFIVGFTRGWKLTLVILAISPVLGLSAAVWAKILSSFTDKELLAYAKA 250 wt P-gp  251 GAVAEEVLAAIRTVIAFGGQKKELERYNKNLEEAKRIGIKKAITANISIG 300
G185V    251 GAVAEEVLAAIRTVIAFGGQKKELERYNKNLEEAKRIGIKKAITANISIG 300
I186N    251 GAVAEEVLAAIRTVIAFGGQKKELERYNKNLEEAKRIGIKKAITANISIG 300
8-A4     251 GAVAEEVLAAIRTVIAFGGQKKELERYNKNLEEAKRIGIKKAITANISIG 300
5-C3     251 GAVAEEVLAAIRTVIAFGGQKKELERYNKNLEEAKRIGIKKAITANISIG 300
2-B2     251 GAVAEEVLAAIRTVIAFGGQKKELERYNKNLEEAKRIGIKKAITANISIG 300
2-B1     251 GAVAEEVLAAIRTVIAFGGQKKELERYNKNLEEAKRIGIKKAITANISIG 300
6-C1     251 GAVAEEVLAAIRTVIAFGGQKKELERYNKNLEEAKRIGIKKAITANISIG 300
8-B4     251 GAVAEEVLAAIRTVIAFGGQKKELERYNKNLEEAKRIGIKKAITANISIG 300
EK5      251 GAVAEEVLAAIRTVIAFGGQKKELERYNKNLEEAKRIGIKKAITANISIG 300 wt P-gp  301 AAFLLIYASYALAFWYGTTLVLSGEYSIGQVLTVFFSVLIGAFSVGQASP 350
G185V    301 AAFLLIYASYALAFWYGTTLVLSGEYSIGQVLTVFFSVLIGAFSVGQASP 350
I186N    301 AAFLLIYASYALAFWYGTTLVLSGEYSIGQVLTVFFSVLIGAFSVGQASP 350
8-A4     301 AAFLLIYASYALAFWYGTTLVLSGEYSIGQVLTVFFSVLIGAFSVGQASP 350
5-C3     301 AAFLLIYASYALAFWYGTTLVLSGEYSIGQVLTVFFSVLIGAFSVGQASP 350
2-B2     301 AAFLLIYASYALAFWYGTTLVLSGEYSIGQVLTVFFSVLIGAFSVGQASP 350
2-B1     301 AAFLLIYASYALAFWYGTTLVLSGEYSIGQVLTVFFSVLIGAFSVGQASP 350
6-C1     301 AAFLLIYASYALAFWYGTTLVLSGEYSIGQVLTVFFSVLIGAFSVGQASP 350
8-B4     301 AAFLLIYASYALAFWYGTTLVLSGEYSIGQVLTVFFSVLIGAFSVGQASP 350
EK5      301 AAFLLIYASYALAFWYGTTLVLSGEYSIGQVLTVFFSVLIGAFSVGQASP 350 wt P-gp  351 SIEAFANARGAAYEIFKIIDNKPSIDSYSKSGHKPDNIKGNLEFRNVHFS 400
G185V    351 SIEAFANARGAAYEIFKIIDNKPSIDSYSKSGHKPDNIKGNLEFRNVHFS 400
I186N    351 SIEAFANARGAAYEIFKIIDNKPSIDSYSKSGHKPDNIKGNLEFRNVHFS 400
8-A4     351 SIEAFANARGAAYEIFKIIDNKPSIDSYSKSGHKPDNIKGNLEFRNVHFS 400
5-C3     351 SIEAFANARGAAYEIFKIIDNKPSIDSYSKSGHKPDNIKGNLEFRNVHFS 400
2-B2     351 SIEAFANARGAAYEIFKIIDNKPSIDSYSKSGHKPDNIKGNLEFRNVHFS 400
2-B1     351 SIEAFANARGAAYEIFKIIDNKPSIDSYSKSGHKPDNIKGNLEFRNVHFS 400
6-C1     351 SIEAFANARGAAYEIFKIIDNKPSIDSYSKSGHKPDNIKGNLEFRNVHFS 400
8-B4     351 SIEAFANARGAAYEIFKIIDNKPSIDSYSKSGHKPDNIKGNLEFRNVHFS 400
EK5      351 SIEAFANARGAAYEIFKIIDNKPSIDSYSKSGHKPDNIKGNLEFRNVHFS 400
```

FIG. 3C

```
wt P-gp  401 YPSRKEVKILKGLNLKVQSGQTVALVGNSGCGKSTTVQLMQRLYDPTEGM 450
G185V    401 YPSRKEVKILKGLNLKVQSGQTVALVGNSGCGKSTTVQLMQRLYDPTEGM 450
I186N    401 YPSRKEVKILKGLNLKVQSGQTVALVGNSGCGKSTTVQLMQRLYDPTEGM 450
8-A4     401 YPSRKEVKILKGLNLKVQSGQTVALVGNSGCGKSTTVQLMQRLYDPTEGM 450
5-C3     401 YPSRKEVKILKGLNLKVQSGQTVALVGNSGCGKSTTVQLMQRLYDPTEGM 450
2-B2     401 YPSRKEVKILKGLNLKVQSGQTVALVGNSGCGKSTTVQLMQRLYDPTEGM 450
2-B1     401 YPSRKEVKILKGLNLKVQSGQTVALVGNSGCGKSTTVQLMQRLYDPTEGM 450
6-C1     401 YPSRKEVKILKGLNLKVQSGQTVALVGNSGCGKSTTVQLMQRLYDPTEGM 450
8-B4     401 YPSRKEVKILKGLNLKVQSGQTVALVGNSGCGKSTTVQLMQRLYDPTEGM 450
EK5      401 YPSRKEVKILKGLNLKVQSGQTVALVGNSGCGKSTTVQLMQRLYDPTEGM 450 wt P-gp  451 VSVDGQDIRTINVRFLREIIGVVSQEPVLFATTIAENIRYGRENVTMDEI 500
G185V    451 VSVDGQDIRTINVRFLREIIGVVSQEPVLFATTIAENIRYGRENVTMDEI 500
I186N    451 VSVDGQDIRTINVRFLREIIGVVSQEPVLFATTIAENIRYGRENVTMDEI 500
8-A4     451 VSVDGQDIRTINVRFLREIIGVVSQEPVLFATTIAENIRYGRENVTMDEI 500
5-C3     451 VSVDGQDIRTINVRFLREIIGVVSQEPVLFATTIAENIRYGRENVTMDEI 500
2-B2     451 VSVDGQDIRTINVRFLREIIGVVSQEPVLFATTIAENIRYGRENVTMDEI 500
2-B1     451 VSVDGQDIRTINVRFLREIIGVVSQEPVLFATTIAENIRYGRENVTMDEI 500
6-C1     451 VSVDGQDIRTINVRFLREIIGVVSQEPVLFATTIAENIRYGRENVTMDEI 500
8-B4     451 VSVDGQDIRTINVRFLREIIGVVSQEPVLFATTIAENIRYGRENVTMDEI 500
EK5      451 VSVDGQDIRTINVRFLREIIGVVSQEPVLFATTIAENIRYGRENVTMDEI 500 wt P-gp  501 EKAVKEANAYDFIMKLPHKFDTLVGERGAQLSGGQKQRIAIARALVRNPK 550
G185V    501 EKAVKEANAYDFIMKLPHKFDTLVGERGAQLSGGQKQRIAIARALVRNPK 550
I186N    501 EKAVKEANAYDFIMKLPHKFDTLVGERGAQLSGGQKQRIAIARALVRNPK 550
8-A4     501 EKAVKEANAYDFIMKLPHKFDTLVGERGAQLSGGQKQRIAIARALVRNPK 550
5-C3     501 EKAVKEANAYDFIMKLPHKFDTLVGERGAQLSGGQKQRIAIARALVRNPK 550
2-B2     501 EKAVKEANAYDFIMKLPHKFDTLVGERGAQLSGGQKQRIAIARALVRNPK 550
2-B1     501 EKAVKEANAYDFIMKLPHKFDTLVGERGAQLSGGQKQRIAIARALVRNPK 550
6-C1     501 EKAVKEANAYDFIMKLPHKFDTLVGERGAQLSGGQKQRIAIARALVRNPK 550
8-B4     501 EKAVKEANAYDFIMKLPHKFDTLVGERGAQLSGGQKQRIAIARALVRNPK 550
EK5      501 EKAVKEANAYDFIMKLPHKFDTLVGERGAQLSGGQKQRIAIARALVRNPK 550 wt P-gp  551 ILLLDEATSALDTESEAVVQVALDKARKGRTTIVIAHRLSTVRNADVIAG 600
G185V    551 ILLLDEATSALDTESEAVVQVALDKARKGRTTIVIAHRLSTVRNADVIAG 600
I186N    551 ILLLDEATSALDTESEAVVQVALDKARKGRTTIVIAHRLSTVRNADVIAG 600
8-A4     551 ILLLDEATSALDTESEAVVQVALDKARKGRTTIVIAHRLSTVRNADVIAG 600
5-C3     551 ILLLDEATSALDTESEAVVQVALDKARKGRTTIVIAHRLSTVRNADVIAG 600
2-B2     551 ILLLDEATSALDTESEAVVQVALDKARKGRTTIVIAHRLSTVRNADVIAG 600
2-B1     551 ILLLDEATSALDTESEAVVQVALDKARKGRTTIVIAHRLSTVRNADVIAG 600
6-C1     551 ILLLDEATSALDTESEAVVQVALDKARKGRTTIVIAHRLSTVRNADVIAG 600
8-B4     551 ILLLDEATSALDTESEAVVQVALDKARKGRTTIVIAHRLSTVRNADVIAG 600
EK5      551 ILLLDEATSALDTESEAVVQVALDKARKGRTTIVIAHRLSTVRNADVIAG 600
```

FIG. 3D

```
wt P-gp   601  FDDGVIVEKGNHDELMKEKGIYFKLVTMQTAGNEVELENAADESKSEIDA  650
G185V     601  FDDGVIVEKGNHDELMKEKGIYFKLVTMQTAGNEVELENAADESKSEIDA  650
I186N     601  FDDGVIVEKGNHDELMKEKGIYFKLVTMQTAGNEVELENAADESKSEIDA  650
8-A4      601  FDDGVIVEKGNHDELMKEKGIYFKLVTMQTAGNEVELENAADESKSEIDA  650
5-C3      601  FDDGVIVEKGNHDELMKEKGIYFKLVTMQTAGNEVELENAADESKSEIDA  650
2-B2      601  FDDGVIVEKGNHDELMKEKGIYFKLVTMQTAGNEVELENAADESKSEIDA  650
2-B1      601  FDDGVIVEKGNHDELMKEKGIYFKLVTMQTAGNEVELENAADESKSEIDA  650
6-C1      601  FDDGVIVEKGNHDELMKEKGIYFKLVTMQTAGNKVKLENAADESKSEIDA  650
8-B4      601  FDDGVIVEKGNHDELMKEKGIYFKLVTMQTAGNEVELENAADKSKSKIDA  650
EK5       601  FDDGVIVEKGNHDELMKEKGIYFKLVTMQTAGNKVKLENAADKSKSKIDA  650 wt P-gp   651  LEMSSNDSRSSLIRKRSTRRSVRGSQAQDRKLSTKEALDESIPPVSFWRI  700
G185V     651  LEMSSNDSRSSLIRKRSTRRSVRGSQAQDRKLSTKEALDESIPPVSFWRI  700
I186N     651  LEMSSNDSRSSLIRKRSTRRSVRGSQAQDRKLSTKEALDESIPPVSFWRI  700
8-A4      651  LEMSSNDSRSSLIRKRSTRRSVRGSQAQDRKLSTKEALDESIPPVSFWRI  700
5-C3      651  LEMSSNDSRSSLIRKRSTRRSVRGSQAQDRKLSTKEALDESIPPVSFWRI  700
2-B2      651  LEMSSNDSRSSLIRKRSTRRSVRGSQAQDRKLSTKEALDESIPPVSFWRI  700
2-B1      651  LEMSSNDSRSSLIRKRSTRRSVRGSQAQDRKLSTKEALDESIPPVSFWRI  700
6-C1      651  LEMSSNDSRSSLIRKRSTRRSVRGSQAQDRKLSTKEALDESIPPVSFWRI  700
8-B4      651  LKMSSNDSRSSLIRKRSTRRSVRGSQAQDRKLSTKEALDESIPPVSFWRI  700
EK5       651  LKMSSNDSRSSLIRKRSTRRSVRGSQAQDRKLSTKEALDESIPPVSFWRI  700 wt P-gp   701  MKLNLTEWPYFVVGVFCAIINGGLQPAFAIIFSKIIGVFTRIDDPETKRQ  750
G185V     701  MKLNLTEWPYFVVGVFCAIINGGLQPAFAIIFSKIIGVFTRIDDPETKRQ  750
I186N     701  MKLNLTEWPYFVVGVFCAIINGGLQPAFAIIFSKIIGVFTRIDDPETKRQ  750
8-A4      701  MKLNLTEWPYFVVGVFCAIINGGLQPAFAIIFSKIIGVFTRIDDPETKRQ  750
5-C3      701  MKLNLTEWPYFVVGVFCAIINGGLQPAFAIIFSKIIGVFTRIDDPETKRQ  750
2-B2      701  MKLNLTEWPYFVVGVFCAIINGGLQPAFAIIFSKIIGVFTRIDDPETKRQ  750
2-B1      701  MKLNLTEWPYFVVGVFCAIINGGLQPAFAIIFSKIIGVFTRIDDPETKRQ  750
6-C1      701  MKLNLTEWPYFVVGVFCAIINGGLQPAFAIIFSKIIGVFTRIDDPETKRQ  750
8-B4      701  MKLNLTEWPYFVVGVFCAIINGGLQPAFAILFSKIIGVFTRIDDPETKRQ  750
EK5       701  MKLNLTEWPYFVVGVFCAIINGGLQPAFAIIFSKIIGVFTRIDDPETKRQ  750 wt P-gp   751  NSNLFSLLFLALGIISFITFFLQGFTFGKAGEILTKRLRYMVFRSMLRQD  800
G185V     751  NSNLFSLLFLALGIISFITFFLQGFTFGKAGEILTKRLRYMVFRSMLRQD  800
I186N     751  NSNLFSLLFLALGIISFITFFLQGFTFGKAGEILTKRLRYMVFRSMLRQD  800
8-A4      751  NSNLFSLLFLALGIISFITFFLQGFTFGKAGEILTKRLRYMVFRSMLRQD  800
5-C3      751  NSNLFSLLFLALGIISFITFFLQGFTFGKAGEILTKRLRYMVFRSMLRQD  800
2-B2      751  NSNLFSLLFLALWIISFITFFLQGFTFGKAGEILTKRLRYMVFRSMLRQD  800
2-B1      751  NSNLFSLLFLALGIISFITFFLQGFTFGKAGEILTKRLRYMVFRSMLRQD  800
6-C1      751  NSNLFSLLFLALGIISFITFFLQGFTFGKAGEILTKRLRYMVFRSMLRQD  800
8-B4      751  NSNLFSLLFLALGIISFITFFLQGFTFGKAGEILTKRLRYMVFRSMLRQD  800
EK5       751  NSNLFSLLFLALGIISFITFFLQGFTFGKAGEILTKRLRYMVFRSMLRQD  800
```

FIG. 3E

```
wt P-gp  801 VSWFDDPKNTTGALTTRLANDAAQVKGAIGSRLAVITQNIANLGTGIIIS 850
G185V    801 VSWFDDPKNTTGALTTRLANDAAQVKGAIGSRLAVITQNIANLGTGIIIS 850
I186N    801 VSWFDDPKNTTGALTTRLANDAAQVKGAIGSRLAVITQNIANLGTGIIIS 850
8-A4     801 VSWFDDPKNTTGALTTRLANDAAQVKGAIGSRLAVITQNIANLGTGIIIS 850
5-C3     801 VSWFDDPKNTTGALTTRLANDAAQVKGAIGSRLAVITQNIANLGTGIIIS 850
2-B2     801 VSWFDDPKNTTGALTTRLANDAAQVKGAIGSRLAVITQNIANLGTGIIIS 850
2-B1     801 VSWFDDPKNTTGALTTRLANDAAQVKGAIGSRLAVITQNIANLETGIIIS 850
6-C1     801 VSWFDDPKNTTGALTTRLANDAAQVKGAIGSRLAVITQNIANLGTGIIIS 850
8-B4     801 VSWFDDPKNTTGALTTRLANDAAQVKGAIGSRLAVITQNIANLGTGIIIS 850
EK5      801 VSWFDDPKNTTGALTTRLANDAAQVKGAIGSRLAVITQNIANLGTGIIIS 850 wt P-gp  851 FIYGWQLTLLLLAIVPIIAIAGVVEMKMLSGQALKDKKELEGAGKIATEA 900
G185V    851 FIYGWQLTLLLLAIVPIIAIAGVVEMKMLSGQALKDKKELEGAGKIATEA 900
I186N    851 FIYGWQLTLLLLAIVPIIAIAGVVEMKMLSGQALKDKKELEGAGKIATEA 900
8-A4     851 FIYGWQLTLLLLAIVPIIAIAGVVEMKMLSGQALKDKKELEGAGKIATEA 900
5-C3     851 FIYGWQLTLLLLAIVPIIAIAGVVEMKMLSGQALKDKKELEGAGKIATEA 900
2-B2     851 FIYGWQLTLLLLAIVPIIAIAGVVEMKMLSGQALKDKKELEGAGKIATEA 900
2-B1     851 FIYGWQLTLLLLAIVPIIAIAGVVEMKMLSGQALKDKKELEGAGKIATEA 900
6-C1     851 FIYGWQLTLLLLAIVPIIAIAGVVEMKMLSGQALKDKKELEGAGKIATEA 900
8-B4     851 FIYGWQLTLLLLAIVPIIAIAGVVEMKMLSGQALKDKKELEGAGKIATEA 900
EK5      851 FIYGWQLTLLLLAIVPIIAIAGVVEMKMLSGQALKDKKELEGAGKIATEA 900 wt P-gp  901 IENFRTVVSLTQEQKFEHMYAQSLQVPYRNSLRKAHIFGITFSFTQAMMY 950
G185V    901 IENFRTVVSLTQEQKFEHMYAQSLQVPYRNSLRKAHIFGITFSFTQAMMY 950
I186N    901 IENFRTVVSLTQEQKFEHMYAQSLQVPYRNSLRKAHIFGITFSFTQAMMY 950
8-A4     901 IENFRTVVSLTQEQKFEHMYAQSLQVPYRNSLRKAHIFGITFSFTQAMMY 950
5-C3     901 IENFRTVVSLTQEQKFEHMYAQSLQVPYRNSLRKAHIFGITFSFTQAMMY 950
2-B2     901 IENFRTVVSLTQEQKFEHMYAQSLQVPYRNSLRKAHIFGITFSFTQAMMY 950
2-B1     901 IENFRTVVSLTQEQKFEHMYAQSLQVPYRNSLRKAHIFGITFSFTQAMMY 950
6-C1     901 IENFRTVVSLTQEQKFEHMYAQSLQVPYRNSLRKAHIFGITFSFTQAMMY 950
8-B4     901 IENFRTVVSLTQEQKFEHMYAQSLQVPYRNSLRKAHIFGITFSFTQAMMY 950
EK5      901 IENFRTVVSLTQEQKFEHMYAQSLQVPYRNSLRKAHIFGITFSFTQAMMY 950 wt P-gp  951 FSYAGCFRFGAYLVAHKLMSFEDVLLVFSAVVFGAMAVGQVSSFAPDYAK 1000
G185V    951 FSYAGCFRFGAYLVAHKLMSFEDVLLVFSAVVFGAMAVGQVSSFAPDYAK 1000
I186N    951 FSYAGCFRFGAYLVAHKLMSFEDVLLVFSAVVFGAMAVGQVSSFAPDYAK 1000
8-A4     951 FSYAGCFRFGAYLVAHKLMSFEDVLLVFSAVVFGAMAVGQVSSFAPDYAK 1000
5-C3     951 FSYAGCFRFGAYLVAHKLMSFEDVLLVFSAVVFGAMAVGQVSSFAPDYAK 1000
2-B2     951 FSYAGCFRFGAYLVAHKLMSFEDVLLVFSAVVFGAMAVGQVSSFAPDYAK 1000
2-B1     951 FSYAGCFRFGAYLVAHKLMSFEDVLLVFSAVVFGAMAVGQVSSFAPDYAK 1000
6-C1     951 FSYAGCFRFGAYLVAHKLMSFEDVLLVFSAVVFGAMAVGQVSSFAPDYAK 1000
8-B4     951 FSYAGCFRFGAYLVAHKLMSFEDVLLVFSAVVFGAMAVGQVSSFAPDYAK 1000
EK5      951 FSYAGCFRFGAYLVAHKLMSFEDVLLVFSAVVFGAMAVGQVSSFAPDYAK 1000
```

FIG. 3F

```
wt P-gp  1001  AKISAAHIIMIIEKTPLIDSYSTEGLMPNTLEGNVTFGEVVFNYPTRPDI  1050
G185V    1001  AKISAAHIIMIIEKTPLIDSYSTEGLMPNTLEGNVTFGEVVFNYPTRPDI  1050
I186N    1001  AKISAAHIIMIIEKTPLIDSYSTEGLMPNTLEGNVTFGEVVFNYPTRPDI  1050
8-A4     1001  AKISAAHIIMIIEKTPLIDSYSTEGLMPNTLEGNVTFGEVVFNYPTRPDI  1050
5-C3     1001  AKISAAHIIMIIEKTPLIDSYSTEGLMPNTLEGNVTFGEVVFNYPTRPDI  1050
2-B2     1001  AKISAAHIIMIIEKTPLIDSYSTEGLMPNTLEGNVTFGEVVFNYPTRPDI  1050
2-B1     1001  AKISAAHIIMIIEKTPLIDSYSTEGLMPNTLEGNVTFGEVVFNYPTRPDI  1050
6-C1     1001  AKISAAHIIMIIEKTPLIDSYSTEGLMPNTLEGNVTFGEVVFNYPTRPDI  1050
8-B4     1001  AKISAAHIIMIIEKTPLIDSYSTEGLMPNTLEGNVTFGEVVFNYPTRPDI  1050
EK5      1001  AKISAAHIIMIIEKTPLIDSYSTEGLMPNTLEGNVTFGEVVFNYPTRPDI  1050 wt P-gp  1051  PVLQGLSLEVKKGQTLALVGSSGCGKSTVVQLLERFYDPLAGKVLLDGKE  1100
G185V    1051  PVLQGLSLEVKKGQTLALVGSSGCGKSTVVQLLERFYDPLAGKVLLDGKE  1100
I186N    1051  PVLQGLSLEVKKGQTLALVGSSGCGKSTVVQLLERFYDPLAGKVLLDGKE  1100
8-A4     1051  PVLQGLSLEVKKGQTLALVGSSGCGKSTVVQLLERFYDPLAGKVLLDGKE  1100
5-C3     1051  PVLQGLSLEVKKGQTLALVGSSGCGKSTVVQLLERFYDPLAGKVLLDGKE  1100
2-B2     1051  PVLQGLSLEVKKGQTLALVGSSGCGKSTVVQLLERFYDPLAGKVLLDGKE  1100
2-B1     1051  PVLQGLSLEVKKGQTLALVGSSGCGKSTVVQLLERFYDPLAGKVLLDGKE  1100
6-C1     1051  PVLQGLSLEVKKGQTLALVGSSGCGKSTVVQLLERFYDPLAGKVLLDGKE  1100
8-B4     1051  PVLQGLSLEVKKGQTLALVGSSGCGKSTVVQLLERFYDPLAGKVLLDGKE  1100
EK5      1051  PVLQGLSLEVKKGQTLALVGSSGCGKSTVVQLLERFYDPLAGKVLLDGKE  1100 wt P-gp  1101  IKRLNVQWLRAHLGIVSQEPILFDCSIAENIAYGDNSRVVSQEEIVRAAK  1150
G185V    1101  IKRLNVQWLRAHLGIVSQEPILFDCSIAENIAYGDNSRVVSQEEIVRAAK  1150
I186N    1101  IKRLNVQWLRAHLGIVSQEPILFDCSIAENIAYGDNSRVVSQEEIVRAAK  1150
8-A4     1101  IKRLNVQWLRAHLGIVSQEPILFDCSIAENIAYGDNSRVVSQEEIVRAAK  1150
5-C3     1101  IKRLNVQWLRAHLGIVSQEPILFDCSIAENIAYGDNSRVVSQEEIVRAAK  1150
2-B2     1101  IKRLNVQWLRAHLGIVSQEPILFDCSIAENIAYGDNSRVVSQEEIVRAAK  1150
2-B1     1101  IKRLNVQWLRAHLGIVSQEPILFDCSIAENIAYGDNSRVVSQEEIVRAAK  1150
6-C1     1101  IKRLNVQWLRAHLGIVSQEPILFDCSIAENIAYGDNSRVVSQEEIVRAAK  1150
8-B4     1101  IKRLNVQWLRAHLGIVSQEPILFDCSIAENIAYGDNSRVVSQEEIVRAAK  1150
EK5      1101  IKRLNVQWLRAHLGIVSQEPILFDCSIAENIAYGDNSRVVSQEEIVRAAK  1150 wt P-gp  1151  EANIHAFIESLPNKYSTKVGDKGTQLSGGQKQRIAIARALVRQPHILLLD  1200
G185V    1151  EANIHAFIESLPNKYSTKVGDKGTQLSGGQKQRIAIARALVRQPHILLLD  1200
I186N    1151  EANIHAFIESLPNKYSTKVGDKGTQLSGGQKQRIAIARALVRQPHILLLD  1200
8-A4     1151  EANIHAFIESLPNKYSTKVGDKGTQLSGGQKQRIAIARALVRQPHILLLD  1200
5-C3     1151  EANIHAFIESLPNKYSTKVGDKGTQLSGGQKQRIAIARALVRQPHILLLD  1200
2-B2     1151  EANIHAFIESLPNKYSTKVGDKGTQLSGGQKQRIAIARALVRQPHILLLD  1200
2-B1     1151  EANIHAFIESLPNKYSTKVGDKGTQLSGGQKQRIAIARALVRQPHILLLD  1200
6-C1     1151  EANIHAFIESLPNKYSTKVGDKGTQLSGGQKQRIAIARALVRQPHILLLD  1200
8-B4     1151  EANIHAFIESLPNKYSTKVGDKGTQLSGGQKQRIAIARALVRQPHILLLD  1200
EK5      1151  EANIHAFIESLPNKYSTKVGDKGTQLSGGQKQRIAIARALVRQPHILLLD  1200
```

FIG. 3G

```
wt P-gp   1201 EATSALDTESEKVVQEALDKAREGRTCIVIAHRLSTIQNADLIVVFQNGR 1250
G185V     1201 EATSALDTESEKVVQEALDKAREGRTCIVIAHRLSTIQNADLIVVFQNGR 1250
I186N     1201 EATSALDTESEKVVQEALDKAREGRTCIVIAHRLSTIQNADLIVVFQNGR 1250
8-A4      1201 EATSALDTESEKVVQEALDKAREGRTCIVIAHRLSTIQNADLIVVFQNGR 1250
5-C3      1201 EATSALDTESEKVVQEALDKAREGRTCIVIAHRLSTIQNADLIVVFQNGR 1250
2-B2      1201 EATSALDTESEKVVQEALDKAREGRTCIVIAHRLSTIQNADLIVVFQNGR 1250
2-B1      1201 EATSALDTESEKVVQEALDKAREGRTCIVIAHRLSTIQNADLIVVFQNGR 1250
6-C1      1201 EATSALDTESEKVVQEALDKAREGRTCIVIAHRLSTIQNADLIVVFQNGR 1250
8-B4      1201 EATSALDTESEKVVQEALDKAREGRTCIVIAHRLSTIQNADLIVVFQNGR 1250
EK5       1201 EATSALDTESEKVVQEALDKAREGRTCIVIAHRLSTIQNADLIVVFQNGR 1250 wt P-gp   1251 VKEHGTHQQLLAQKGIYFSMVSVQAGTKRQ 1280
G185V     1251 VKEHGTHQQLLAQKGIYFSMVSVQAGTKRQ 1280
I186N     1251 VKEHGTHQQLLAQKGIYFSMVSVQAGTKRQ 1280
8-A4      1251 VKEHGTHQQLLAQKGIYFSMVSVQAGTKRQ 1280
5-C3      1251 VKEHGTHQQLLAQKGIYFSMVSVQAGTKRQ 1280
2-B2      1251 VKEHGTHQQLLAQKGIYFSMVSVQAGTKRQ 1280
2-B1      1251 VKEHGTHQQLLAQKGIYFSMVSVQAGTKRQ 1280
6-C1      1251 VKEHGTHQQLLAQKGIYFSMVSVQAGTKRQ 1280
8-B4      1251 VKEHGTHQQLLAQKGIYFSMVSVQAGTKRQ 1280
EK5       1251 VKEHGTHQQLLAQKGIYFSMVSVQAGTKRQ 1280
```

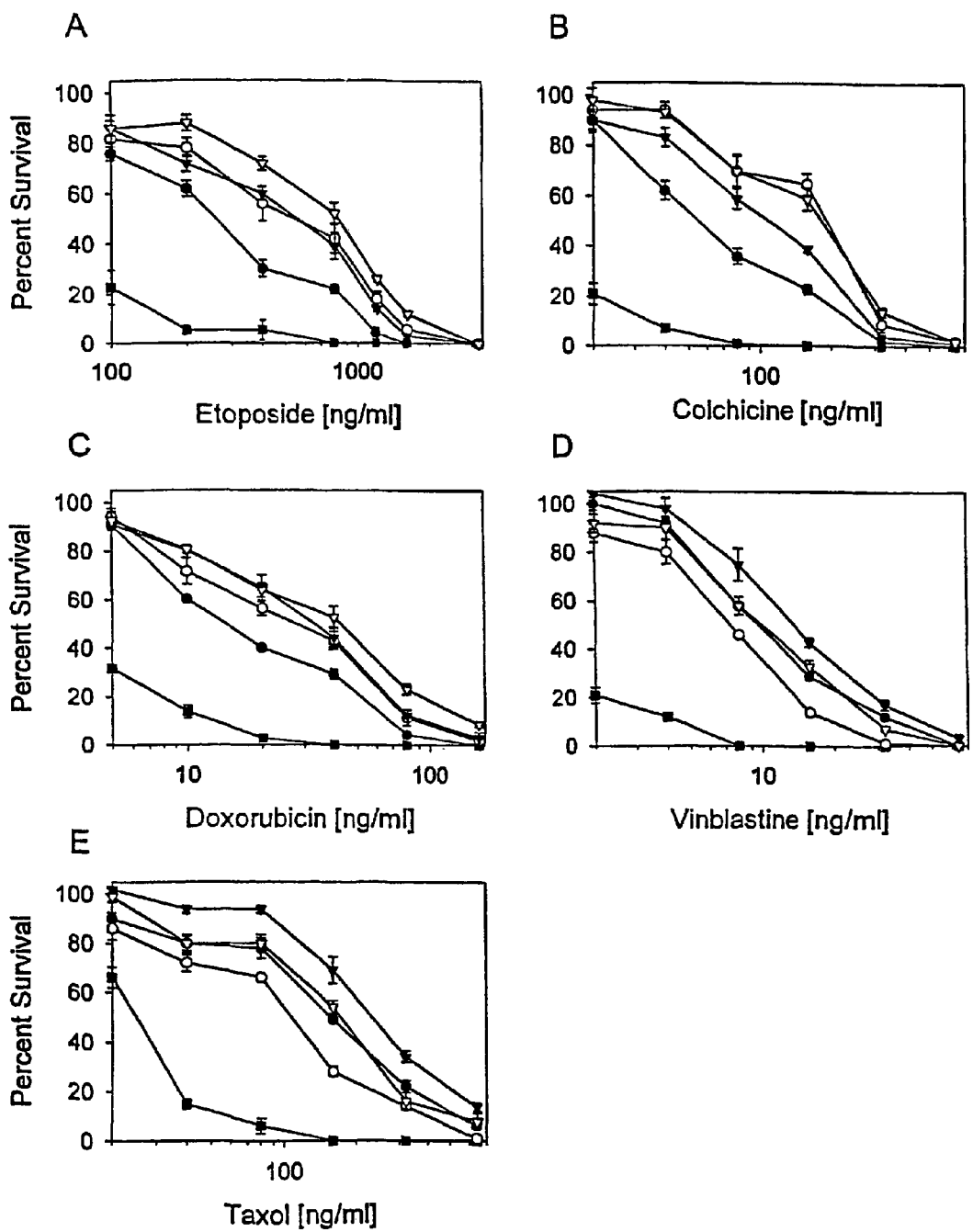

FIG. 5
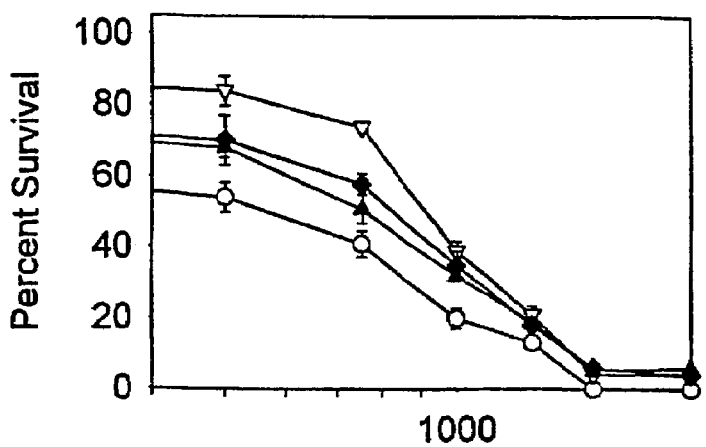
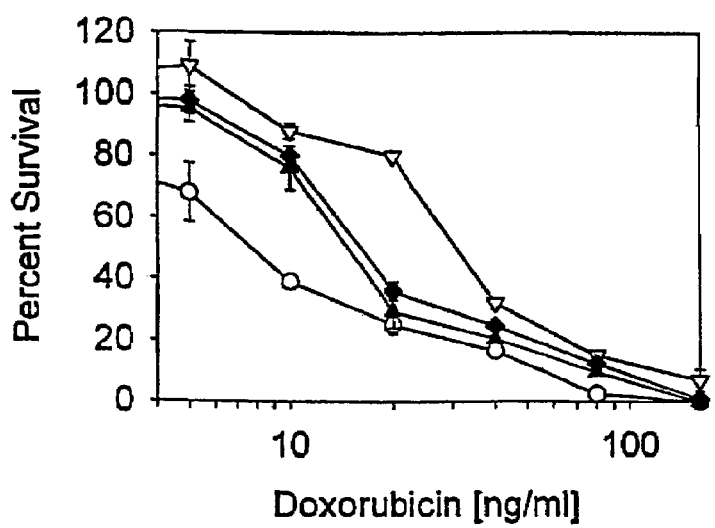
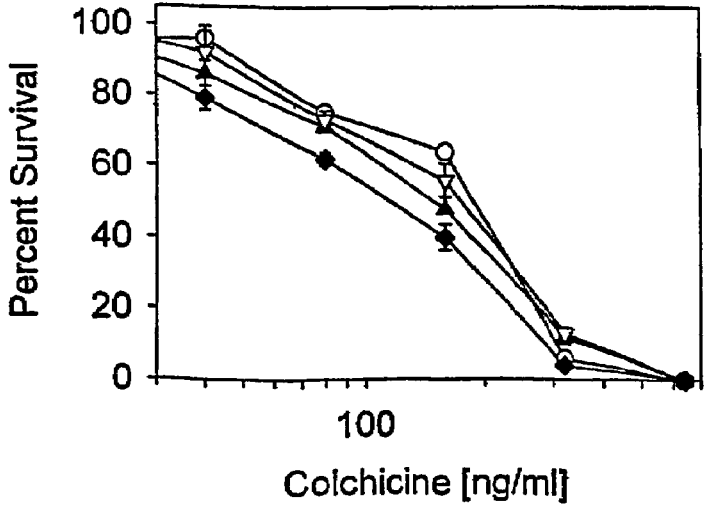

MUTATIONS OF THE MDR1 P-GLYCOPROTEIN THAT IMPROVES ITS ABILITY TO CONFER RESISTANCE TO CHEMOTHERAPEUTIC DRUGS

This application claims the benefit of priority from U.S. Provisional Patent Application No. 60/222,313, filed on Aug. 1, 2000, the disclosure of which is explicitly incorporated by reference herein.

STATEMENT OF GOVERNMENT INTEREST

This invention was made with government support under grants CA-040333 by the National Institutes of Health. The government has certain rights in the invention.

BACKGROUND OF THE INVENTION

1. Field of the Invention

The invention relates to mutant human P-glycoprotein polypeptides that confer increased resistance to certain chemotherapeutic drugs compared to wild-type P-glycoprotein or P-glycoprotein having a glycine to valine substitution at position 185, and nucleic acid molecules encoding the same. The invention also relates to antibodies that specifically bind mutant human P-glycoproteins. The invention further relates to methods for diagnosis and treatment of conditions associated with P-glycoprotein-mediated multidrug resistance.

2. Background of the Invention

Multidrug resistance (MDR) is a phenomenon in which a cell becomes resistant to a large group of structurally diverse chemotherapeutic drugs that act at different intracellular targets. One mechanism of MDR1 in clinical cancer is active drug efflux mediated by a cellular protein termed P-glycoprotein. P-glycoprotein is an integral membrane protein having six transmembrane domains and consisting of 1280 amino acids (SEQ ID NO: 2), which functions as a broad specificity efflux pump. The protein is composed of two structurally similar portions, of approximately 600 amino acids each, which are separated by a linker region. Human P-glycoprotein is encoded by the MDR1 gene (Chen et al., 1986, *Cell* 47:381-89), the wild-type cDNA sequence of which is identified herein as SEQ ID NO: 1.

A number of mutant P-glycoproteins, possessing an altered ability to transport different drugs, have been isolated. Most of these mutants show decreased drug efflux, while only a small number of mutants exhibit increased drug transport. Examples of the latter group are the MDR1-G185V (Choi et al., 1988, *Cell* 53:519-29; Safa et al., 1990, *Proc. Natl. Acad. Sci. U.S.A.* 87:7225-29) and MDR1-H61F mutants (Taguchi et al., 1997, *Biochemistry* 36:8883-89). Mutant P-glycoproteins showing increased resistance to certain chemotherapeutic drugs also show decreased resistance to other drugs.

Efforts to treat clinical cancer with cytotoxic drugs are often hampered by sensitivity of non-cancerous proliferating cells, such as hematopoietic cells, to the cytotoxic effects of these drugs. One approach to overcoming this shortcoming is to genetically engineer hematopoietic cells, particularly precursor cells such as stem cells, to express elevated levels of P-glycoprotein in order to make these cells more resistant to the cytotoxic effects of chemotherapeutic drugs, enabling higher doses of such drugs to be administered for more effective anticancer treatment. These efforts would be even more effective if the non-cancerous cells could be made preferentially resistant to a chemotherapeutic drug that was particularly appropriate for treatment of a specific cancer.

Additionally, expression of different mutant P-glycoproteins in clinical cancer can make inappropriate a specific choice of chemotherapeutic drug in an individual patient having a neoplastic disease conventionally treated with said specific drug. Identification of specific mutants in clinical cancer would provide clinicians with information enabling rational, individualized drug treatment choices in anticancer treatment.

Thus, there remains a need in the art for mutant P-glycoproteins that confer increased resistance to certain chemotherapeutic drugs relative to wild-type P-glycoprotein or P-glycoprotein having a glycine to valine substitution at position 185. The development of such mutants would have wide application in the treatment and diagnosis of cancer.

SUMMARY OF THE INVENTION

The present invention provides nucleic acid molecules encoding mutant human P-glycoprotein polypeptides that confer increased resistance to certain chemotherapeutic drugs compared to wild-type P-glycoprotein or P-glycoprotein having a glycine to valine substitution at position 185.

Specifically, the present invention provides a nucleic acid molecule comprising a nucleotide sequence encoding a mutant human P-glycoprotein having either an asparagine substitution at position 186, a phenylalanine substitution at position 56, phenylalanine substitutions at positions 190 and 197, a tryptophan substitution at position 763, a glutamic acid substitution at position 844, lysine substitutions at positions 634 and 636, lysine substitutions at positions 643, 647, and 652, or lysine substitutions at positions 634, 636, 643, 647, and 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention also provides a nucleic acid molecule comprising a nucleotide sequence encoding a mutant human P-glycoprotein having either a phenylalanine substitution at position 190; a phenylalanine substitution at position 197; a lysine substitution at position 634; a lysine substitution at position 636; a lysine substitution at position 643; a lysine substitution at position 647; or a lysine substitution at position 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention further provides a nucleic acid molecule comprising a nucleotide sequence encoding a mutant human P-glycoprotein having at least one amino acid substitution selected from the group consisting of: an asparagine substitution at position 186; a phenylalanine substitution at position 56; phenylalanine substitutions at positions 190 and 197; a tryptophan substitution at position 763; a glutamic acid substitution at position 844; lysine substitutions at positions 634 and 636; and lysine substitutions at positions 643, 647, and 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention still further provides a nucleic acid molecule comprising a nucleotide sequence encoding a mutant human P-glycoprotein having at least one amino acid substitution selected from the group consisting of: an asparagine substitution at position 186, a phenylalanine substitution at position 56; a phenylalanine substitution at position 190; a phenylalanine substitution at position 197; a tryptophan substitution at position 763, a glutamic acid substitution at position 844, a lysine substitution at position 634; a lysine substitution at position 636; a lysine substitution at position 643; a lysine substitution at position 647; or a lysine substitution at position 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention also provides a nucleic acid molecule comprising a nucleotide sequence encoding a polypeptide as set forth in any of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

The present invention further provides a nucleic acid molecule comprising a nucleotide sequence encoding a polypeptide as set forth in SEQ ID NO: 2 having at least one amino acid substitution selected from the group consisting of: an asparagine substitution at position 186; a phenylalanine substitution at position 56; phenylalanine substitutions at positions 190 and 197; a tryptophan substitution at position 763; a glutamic acid substitution at position 844; lysine substitutions at positions 634 and 636; and lysine substitutions at positions 643, 647, and 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention still further provides a nucleic acid molecule comprising a nucleotide sequence encoding a polypeptide as set forth in SEQ ID NO: 2 having at least one amino acid substitution selected from the group consisting of: an asparagine substitution at position 186, a phenylalanine substitution at position 56; a phenylalanine substitution at position 190; a phenylalanine substitution at position 197; a tryptophan substitution at position 763, a glutamic acid substitution at position 844, a lysine substitution at position 634; a lysine substitution at position 636; a lysine substitution at position 643; a lysine substitution at position 647; or a lysine substitution at position 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The nucleic acid molecules of the present invention may also encode mutant P-glycoproteins that have a valine substitution at position 185 in addition to the one or multiplicity of the specific amino acid substitutions disclosed herein.

The present invention also provides for an expression vector comprising the isolated nucleic acid molecules as set forth herein and recombinant host cells comprising the recombinant nucleic acid molecules as set forth herein.

The present invention also provides mutant human P-glycoproteins that confer increased resistance to certain chemotherapeutic drugs relative to wild-type P-glycoprotein or P-glycoprotein having a glycine to valine substitution at position 185.

Specifically, the present invention provides a mutant human P-glycoprotein having either an asparagine substitution at position 186 (SEQ ID NO: 4), a phenylalanine substitution at position 56 (SEQ ID NO: 5), phenylalanine substitutions at positions 190 and 197 (SEQ ID NO: 6), a tryptophan substitution at position 763 (SEQ ID NO: 7), a glutamic acid substitution at position 844 (SEQ ID NO: 8), lysine substitutions at positions 634 and 636 (SEQ ID NO: 9), lysine substitutions at positions 643, 647, and 652 (SEQ ID NO: 10), or lysine substitutions at positions 634, 636, 643, 647, and 652 (SEQ ID NO: 11), wherein expression of each of these mutant P-glycoproteins in mammalian cells confers increased resistance to certain chemotherapeutic drugs compared to wild-type P- glycoprotein (SEQ ID NO: 2) or P-glycoprotein having a glycine to valine substitution at position 185 (SEQ ID NO: 3).

The present invention also provides a mutant human P-glycoprotein having either a phenylalanine substitution at position 190 (SEQ ID NO: 12); a phenylalanine substitution at position 197 (SEQ ID NO: 13); a lysine substitution at position 634 (SEQ ID NO: 14); a lysine substitution at position 636 (SEQ ID NO: 15); a lysine substitution at position 643 SEQ ID NO: 16); a lysine substitution at position 647 (SEQ ID NO: 17); or a lysine substitution at position 652 (SEQ ID NO: 18), wherein expression of each of these mutant P- glycoproteins in mammalian cells confers increased resistance to certain chemotherapeutic drugs compared to wild-type P-glycoprotein (SEQ ID NO: 2) or P-glycoprotein having a glycine to valine substitution at position 185 (SEQ ID NO: 3).

The present invention further provides a mutant human P-glycoprotein having at least one amino acid substitution selected from the group consisting of: an asparagine substitution at position 186; a phenylalanine substitution at position 56; phenylalanine substitutions at positions 190 and 197; a tryptophan substitution at position 763; a glutamic acid substitution at position 844; lysine substitutions at positions 634 and 636; and lysine substitutions at positions 643, 647, and 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention still further provides a mutant human P-glycoprotein having at least one amino acid substitution selected from the group consisting of: an asparagine substitution at position 186, a phenylalanine substitution at position 56; a phenylalanine substitution at position 190; a phenylalanine substitution at position 197; a tryptophan substitution at position 763, a glutamic acid substitution at position 844, a lysine substitution at position 634; a lysine substitution at position 636; a lysine substitution at position 643; a lysine substitution at position 647; or a lysine substitution at position 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention also provides a polypeptide as set forth in any of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

The present invention further provides a polypeptide as set forth in SEQ ID NO: 2 having at least one amino acid substitution selected from the group consisting of: an asparagine substitution at position 186; a phenylalanine substitution at position 56; phenylalanine substitutions at positions 190 and 197; a tryptophan substitution at position 763; a glutamic acid substitution at position 844; lysine substitutions at positions 634 and 636; and lysine substitutions at positions 643, 647, and 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The present invention still further provides a polypeptide as set forth in SEQ ID NO: 2 having at least one amino acid substitution selected from the group consisting of: an asparagine substitution at position 186, a phenylalanine substitution at position 56; a phenylalanine substitution at position 190; a phenylalanine substitution at position 197; a tryptophan substitution at position 763, a glutamic acid substitution at position 844, a lysine substitution at position 634; a lysine substitution at position 636; a lysine substitution at position 643; a lysine substitution at position 647; or a lysine substitution at position 652, wherein expression of each of these mutant P-glycoproteins in mammalian cells confers increased resistance to certain chemotherapeutic drugs compared to wild-type P-glycoprotein or P-glycoprotein having a glycine to valine substitution at position 185.

The mutant P-glycoproteins of the present invention may also have a valine substitution at position 185 in addition to the one or multiplicity of the specific amino acid substitutions disclosed herein.

The molecules of the present invention are advantageously used for the treatment and diagnosis of cancer. In a preferred embodiment, P-glycoprotein mutants occurring in a clinical tumor sample are identified by immunological assay using an antibody of the invention or antigen-binding fragment thereof specific for said mutant, or by nucleic acid hybridization using a nucleic acid probe specific for said mutant, or by in vitro amplification of mutant-encoding nucleic acid. In further preferred embodiments, a P-glycoprotein mutant of the invention is advantageously introduced into a non-cancerous cell, most preferably a hematopoietic cell, of a human cancer patient, and reintroduced into said patient, thereby permitting increased levels of a particular chemotherapeutic drug (to which the P-glycoprotein mutant specifically confers increased resistance compared to wild-type P-glycoprotein or P-glycoprotein having a glycine to valine substitution at position 185) to be administered to said patient.

Specific preferred embodiments of the present invention will become evident from the following more detailed description of certain preferred embodiments and the claims.

DESCRIPTION OF THE DRAWINGS

FIGS. 3A through 3G illustrate an amino acid sequence alignment of human wild-type P-glycoprotein (wt P-gp; SEQ ID NO: 2) and P-glycoprotein mutants encoded by MDR1-G185V (G185V; SEQ ID NO: 3), MDR1-I186N (I186N; SEQ ID NO: 4), MDR1-L56P (8-A4; SEQ ID NO: 5), MDR1-I190F/M197F (5-C3; SEQ ID NO: 6), MDR1-G763W (2-B2; SEQ ID NO: 7), MDR1-G844E (2-B1; SEQ ID NO: 8), MDR1-E634K/E636K (6-C1; SEQ ID NO: 9),MDR1-E643K/E647K/E652K (8-B4; SEQ ID NO: 10) and MDR1-E634K/E636K/E643K/E647K/E652K (EK5; SEQ ID NO: 11);

FIGS. 4A through 4E illustrate the results of clonogenic assays for resistance to etoposide (panel A), colchicine (panel B), doxorubicin (panel C), vinblastine (panel D), and taxol (panel E) for NIH 3T3 cells transduced with LXSN (closed squares), wild-type MDR1 (closed circles), MDR1-G185V (open circles), MDR1-I186N (closed triangles), or MDR1-G185V/I186N (open triangles);

FIGS. 5A through 5C illustrate the results of clonogenic assays for resistance to etoposide (panel A), doxorubicin (panel B), and colchicine (panel C) for NIH 3T3 cells transduced with LMDR1-G185V (open circles), LMDR1-G185V-EK2 (closed triangles), LMDR1-G185V-EK3 (open triangles), or LMDR1-G185V-EK5 (closed diamonds);

DETAILED DESCRIPTION OF THE PREFERRED EMBODIMENTS

Figure 1:
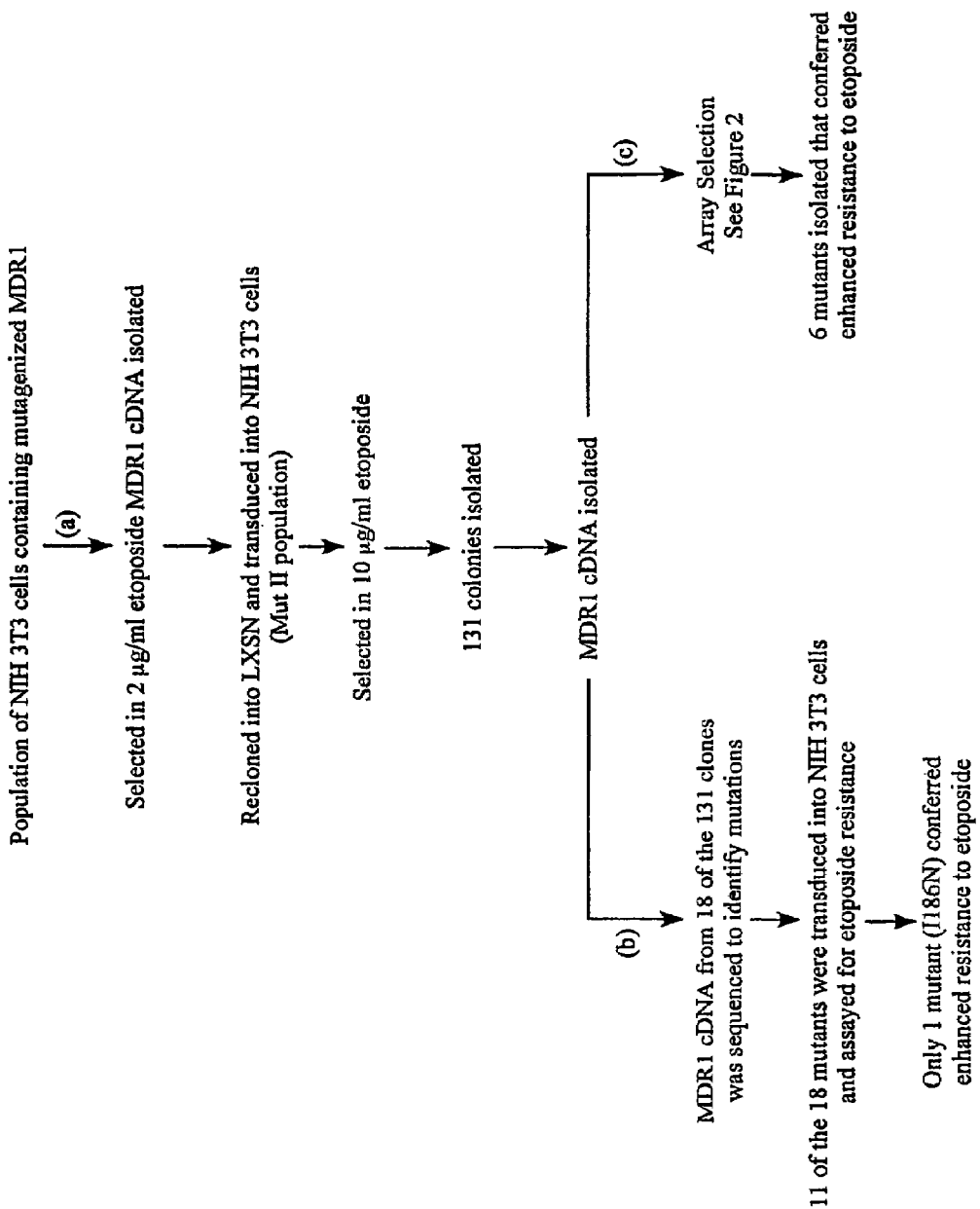
FIG. 1 illustrates the selections that were used to isolate P-glycoprotein mutants conferring enhanced resistance to etoposide.

The present invention provides nucleic acid molecules encoding mutant human P-glycoprotein polypeptides that confer increased resistance to certain chemotherapeutic drugs relative to wild-type P-glycoprotein or P-glycoprotein having a glycine to valine substitution at position 185.

The production of proteins such as the mutant P-glycoproteins of the invention from cloned genes by genetic engineering means is well Known in this art. The discussion that follows is accordingly intended as an overview of this field, and is not intended to reflect the full state of the art.

For the purpose of this invention, "P-glycoprotein" refers to the polypeptide encoded by the human MDR1 gene.

Nucleic acid encoding the mutant P-glycoproteins of this invention can be obtained, in view of the instant disclosure, by chemical synthesis, by screening reverse transcripts of mRNA from tumor cells resistant to MDR-type drugs or cultured cell lines derived therefrom, by screening genomic libraries from appropriate cells, or by combinations of these procedures, as illustrated below. Screening of cDNA prepared from cellular mRNA or genomic DNA may be carried out with full-length, partial or oligonucleotide probes generated from mutant P-glycoprotein nucleotide sequence information provided herein, as discussed above. Probes may be labeled with a detectable group such as a fluorescent group, a radioactive atom or a chemiluminescent group in accordance with known procedures and used in conventional hybridization assays, as described in greater detail in the Examples below. In the alternative, mutant P-glycoprotein encoding nucleic acid can be obtained by use of the polymerase chain reaction (PCR) procedure, with the PCR oligonucleotide primers being produced from the mutant P-glycoprotein nucleotide sequences provided herein. See U.S. Pat. No. 4,683,195 to Mullis et al. and U.S. Pat. No. 4,683,202 to Mullis. In preferred embodiments, ill vitro mutagenesis techniques known in the art and as described herein can be used to produce any of the mutant P-glycoproteins of the invention using cloned human P-glycoprotein-encoding nucleic acid identified herein as SEQ ID NO: 1.

Nucleic acids and oligonucleotides of the present invention are useful as probes for screening DNA libraries to isolate and characterize additional mutant P-glycoproteinencoding nucleic acids of the invention. For the purposes of this invention, these probes are used under high stringency hybridization conditions, defined herein as follows. The probes are labeled with 150 µCi $^{32}$P-ATP and hybridized overnight at 42° C. in a hybridization buffer comprising 6×SSC (0.9 M NaCl, 0.09 M sodium citrate dihydrate, pH 7.0), 2×Denhardt's solution (0.04% Ficoll, 0.04% polyvinylpyrrolidone, 0.04% bovine serum albumin), and 0.25% sodium dodecyl sulfate (SDS). After hybridization, filters are washed four or five times for ten minutes apiece in an excess volume of 6×SSC (0.9 M NaCl, 0.09M sodium citrate dihydrate, pH 7.0) and 0.05% SDS at room temperature. Thereafter, three ten-minute washes are performed one after another in this buffer at temperatures of 55° C., 60° C. and 63° C.

Mutant P-glycoproteins may be synthesized in cells, most preferably cells comprising exogenously-added, recombinant DNA, most preferably cDNA, encoding said proteins. In particular, cells transformed with a recombinant expression construct comprising a nucleic acid encoding a mutant P-glycoprotein of the invention can be used to provide a homogeneous culture of mutant P-glycoprotein expressing cells. Recombinant expression constructs comprising the mutant P-glycoprotein coding sequences as disclosed herein can also be comprised of a vector that is a replicable DNA construct. Vectors are used herein either to amplify DNA encoding a mutant P-glycoprotein and/or to express DNA that encodes a mutant P-glycoprotein. For the purposes of this invention, a recombinant expression construct is a replicable DNA construct in which a DNA sequence encoding mutant P-glycoprotein is operably linked to suitable control sequences capable of effecting the expression of the receptor in a suitable host cell. The need for such control sequences will vary depending upon the host selected and the transformation method chosen. Generally, control sequences include a transcriptional promoter, an optional operator or enhancer sequence to control or regulate transcription, a sequence encoding suitable mRNA ribosomal binding sites, and sequences which control the termination of transcription and translation, and in mammalian cells, sequences that direct 5' terminal capping and 3' terminal polyadenylation of the primary transcript. Amplification vectors, on the other hand, do not require expression control domains. All that is needed is the ability to replicate in a host, usually conferred by an origin of replication, and a selection gene to facilitate recognition of transformants. See, Sambrook et al., 2001, *Molecular Cloning: A Laboratory Manual* (Cold Spring Harbor Press: New York).

Vectors useful for practicing the present invention include plasmids, viruses (including phage), retroviruses, and particularly integratable DNA fragments (i.e., fragments integratable into the host genome by recombination). The vector may replicate and function independently of the host genome, or more preferably, may, in some instances, integrate into the genome itself. Suitable vectors will contain replicon and control sequences which are derived from species compatible with the intended expression host. Transformed host cells are preferably prokaryotic or eukaryotic cells that have been transformed or transfected with recombinant expression constructs made using recombinant DNA techniques and comprising mutant P-glycoprotein-encoding sequences. Preferred host cells are bacterial cells, most preferably *Escherichia coli* cells, mammalian cells, most preferably mammalian cells such as 293 cells, HeLa cells, COS, and CHO cells, and insect cells, most preferably Sf9 cells (using baculoviral vectors). Transformed host cells are chosen that are capable of expressing functional mutant P-glycoproteins introduced using the recombinant expression construct. See, Sambrook et at., ibid.

Homogeneous compositions of the mutant P-glycoproteins are provided by the invention. As used herein, the term "homogeneous" is intended to encompass preparations wherein the mutant P-glycoprotein of the invention is the predominant protein species in the preparation, preferably wherein the mutant P-glycoprotein comprises at least 70%, more preferably wherein the mutant P-glycoprotein comprises from 80-90%, and most preferably where the mutant P-glycoprotein comprises greater than 90% of the protein in the preparation. In preferred embodiments, said preparations have one or a multiplicity of additional protein components wherein no one component comprises more than about 5% and more preferably about 1% of the protein in the preparation.

The invention also provides antibodies that are immunologically reactive to a mutant P-glycoprotein, most preferably human mutant P-glycoproteins explicitly disclosed herein. The antibodies provided by the invention may be raised as follows. First, peptide fragments of the mutant P-glycoproteins of the invention can be chemically synthesized or isolated from the full-length sequence, covalently attached to a carrier molecule such as keyhole limpet hemocyanin, and injected into an appropriate experimental animal. Animals that are used for such inoculations include individuals from species comprising cows, sheep, pigs, mice, rats, rabbits, hamsters, goats and primates. Preferred animals for inoculation are rodents (including mice, rats, and hamsters) and rabbits. For preparing polyclonal antisera, the most preferred animal is rabbit. For preparing monoclonal antibodies, which are preferred, the most preferred animal is the mouse. Antibodies isolated in this manner are tested for binding specificity to identify antibodies that specifically bind mutant P-glycoproteins and do not bind wild-type P-glycoprotein or P-glycoprotein having only a glycine to valine substitution at position 185.

Cells that can be used for such inoculations, or for any of the other means used in the invention, include any cell, clonal isolate, or cell line that expresses a mutant P-glycoprotein or any epitope thereof, most preferably as a result of molecular or genetic engineering. In one embodiment, said recombinant protein is prepared in *E. coli* cells, most preferably having been transformed with a recombinant expression construct comprising a nucleic acid encoding a human mutant P-glycoprotein or epitopes thereof, and that express the mammalian gene product, wherein it is understood that such preparations are sufficiently purified from pyrogenic or other bacterial toxins or contaminants as to be suitable for injection into an animal. In another embodiment, said recombinant protein is prepared in insect cells, preferably Sf9 cells, most preferably having been transformed with a recombinant baculovirus construct comprising a nucleic acid encoding a human mutant P-glycoprotein or epitopes thereof, and that express the mammalian gene product. Additional preferred cells are mammalian cells expressing a mutant P-glycoprotein of the invention or epitope thereof, most preferably a cell that is syngeneic or congeneic with the animal in which the antibody is raised, so as to minimize non-mutant P-glycoprotein-specific immunological responses in said animal.

The present invention provides polyclonal antisera and monoclonal antibodies that are immunologically reactive with an epitope that is a mutant P-glycoprotein or fragment thereof Monoclonal antibodies are the most preferred. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with mutant P-glycoprotein, or cells expressing such a mutant P-glycoprotein, as described above. The myeloma cell lines used in the invention include lines derived from myelomas of mice, rats, hamsters, primates, and humans. Preferred myeloma cell lines are from mouse, and the most preferred mouse myeloma cell line is P3X63-Ag8.653. The animals from which spleens are obtained after immunization are rats, mice, and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a mutant P-glycoprotein.

The present invention encompasses fragments of said antibody that are immunologically reactive with an epitope of a mutant P-glycoprotein. Such fragments are produced by any number of methods known in the art, including but not limited to proteolytic cleavage, chemical synthesis, or preparation of such fragments by means of genetic engineering technology, and include Fab fragments, Fab' fragments, $F(ab)_2$ fragments, and $F_v$ fragments. The present invention also encompasses single-chain antibodies that are immunologically reactive with an epitope of a mutant P-glycoprotein made by methods known to those of skill in the art.

The present invention also encompasses an epitope of a mutant P-glycoprotein that is comprised of sequences, and/ or a conformation of sequences present in the mutant P-glycoprotein molecule. Most preferably, the epitope comprises a peptide comprising at least one mutated amino acid residue compared with wild-type P-glycoprotein or P-glycoprotein having a glycine to valine substitution at position 185. This epitope may be naturally occurring, or may be the result of proteolytic cleavage of the mutant P-glycoprotein molecule and isolation of an epitope-containing peptide or may be obtained by chemical and more preferably automated chemical synthesis of an epitope-containing peptide using methods well known to those skilled in the art. The present invention also encompasses epitope peptides produced as a result of genetic engineering technology and synthesized by genetically engineered cells, preferably prokaryotic cells and most preferably E. coli cells, or by mammalian cells.

The invention also provides methods for screening compounds for the capacity to disrupt binding of cytotoxic drugs with the mutant P-glycoprotein or to disrupt drug efflux from cells expressing said mutant P-glycoprotein. In these methods, drug efflux from cells expressing wild-type P-glycoprotein, P-glycoprotein having a glycine to valine substitution at position 185, and a mutant P-glycoprotein of the invention is compared in the presence and absence of a test compound. In preferred embodiments, drug efflux is determined by cytotoxicity, whereby decreased drug efflux in the presence of the compound is detected by increased cytotoxicity in the presence of a constant concentration of cytotoxic drug. In alternative embodiments, drug efflux is determined using non-toxic compounds that are effluxed by P-glycoprotein, most preferably detectable compounds such as rhodamine.

The mutant P-glycoprotein molecules of the present invention are advantageous for use in treating cancer. One aspect of this advantageous use is in diagnosis, particularly in determining, prior to administration of a chemotherapeutic drug, whether the tumor cells express a mutant P-glycoprotein having increased resistance to a particular chemotherapeutic drug. In the art, clinical trials have developed specific chemotherapeutic drug regimens wherein certain types of clinical cancer are treated with particular cheinotherapeutic drugs, often in combination. The disclosure herein that certain P-glycoprotein mutants are preferentially resistant to certain such chemotherapeutic drugs makes it advantageous to know prior to initiating treatment with a particular drug whether an individual patient's tumor expresses a mutant P-glycoprotein that has increased resistance to said drug. In preferred embodiments, a tumor sample such as a biopsy sample is contacted with an immunological reagent such as an antibody that is specific for the particular mutant P-glycoprotein of the invention having increased resistance to a particular chemotherapeutic drug. In alternative embodiments, the sample is tested using nucleic acid hybridization techniques using probes specific for the particular mutant P-glycoprotein of the invention having increased resistance to a particular chemotherapeutic drug. In a particularly preferred alternative embodiment, the sample is tested using in vitro amplification techniques such as the polymerase chain reaction, using amplification oligonucleotide primers and conditions specific for the particular mutant P-glycoprotein of the invention having increased resistance to a particular chemotherapeutic drug.

Another aspect of the advantageous uses of this invention is in therapy, particularly with regard to protecting non-cancerous proliferating cells in a patient's body, most preferably hematopoietic cells, hair follicles, and epithelial cells of the gastrointestinal tract, from the cytotoxic effects of chemotherapeutic drug administration. As is well appreciated in the art, a consequence of chemotherapeutic drug treatment is the destruction of several classes of non-cancerous proliferating cells, most importantly hematopoietic cells. Frequently the amourit of duration of chemotherapeutic drug treatment is limited by the deleterious effects of chemotherapeutic drugs on hematopoietic cells, resulting inter alia in acute, potentially life-threatening conditions such as leukocytopenia. In one preferred embodiment, the innate resistance of hematopoietic cells to chemotherapeutic drugs is augmented by transducing hematopoietic cells, most preferably hematopoietic stem cells, with a recombinant expression construct encoding a mutant P-glycoprotein of the invention. In this aspect, the mutant P-glycoprotein is chosen to confer on the cell increased resistance to the cytotoxic drug understood and accepted in the art as an appropriate chemotherapeutic agent for the particular cancer. In this aspect, the hematopoietic cells are transduced ex vivo and then returned to the patient, followed thereafter by treatment with greater than conventional amounts of the chemotherapeutic drug to which the hematopoietic cells have been made preferentially resistant by expression of the mutant P-glycoprotein. In another embodiment, homogeneous preparations of mutant P-glycoproteins are delivered to normal cells as polypeptides rather than via gene therapy, for example in liposome-encapsulated form.

The Examples, which follow, are illustrative of specific embodiments of the invention, and various uses thereof. They are set forth for explanatory purposes only, and are not to be taken as limiting the invention.

EXAMPLE 1

Isolation of the Mutant P-glycoprotein Encoded by MDR1-I186N

A population of NIH 3T3 cells expressing a randomly mutagenized human MDR1-G185V gene was prepared as previously described (Roninson et al., 1998, *Methods Enzymol.* 292: 225-48). This population was used to select MDR1-G185V mutants that confer hyper-resistance to etoposide (using the selection scheme shown in FIGS. 1A and 1B).

A portion of the 3T3 cell population covering the complexity of the randomly mutagenized human MDR1-G185V library by approximately one-fold ($1.2 \times 10^7$ cells) was initially selected in 2 μg/mL etoposide. Approximately 1 in 1000 cells (0.1%) survived this selection. Surviving colonies were expanded and pooled, and MDR1 cDNA was rescued and recloned back into the parental vector LXSN as previously described (Roninson et al., 1998, ibid.). The library of rescued MDR1 cDNA, designated Mut II, was then used to transduce naïve NIH 3T3 cells.

The population of NIH 3T3 cells transduced with Mut II was then selected in 10 μg/mL etoposide. The 131 colonies obtained from this selection were expanded and genomic DNA extracted from the clonal lines as previously described (Roninson et al., 1998, ibid.). Mutant MDR1-G185V cDNA prepared using mRNA from eighteen clonal lines was also isolated, sequenced, and analyzed for mutations. A mixture of MDR1 cDNA from all 131 clonal lines was sequenced in both directions, and compared with unmutagenized MDR1-G185V, in order to determine whether particular mutations were heavily represented among the surviving MDR1-G185V mutants.

Mutant MDR1-G185V cDNA isolated from eleven clonal lines was tested for the ability to confer elevated resistance to etoposide as compared to unmutagenized MDR1-G185V. Fragments of MDR1 cDNA containing mutations were first excised from the MDR1 cDNA using restriction endonucleases that recognize appropriate sites flanking the mutation, and then the fragments were recloned into the parental LMDR1-G185V vector. Naïve NIH 3T3 cells were individually transduced with the eleven LMDR1-G185V mutants, wild-type LMDR1-G185V, or LXSN, and then analyzed by FACS for MDR1 expression. Each of the populations containing LMDR1-G185V (either mutant or wild-type) showed a similar level of MDR1 expression, as indicated by staining with the P-glycoprotein-specific antibody UIC2. The cell populations were then assayed for etoposide resistance. Only one of the eleven mutants showed an increased resistance to etoposide as compared to the wild-type MDR1-G185V. Sequence analysis revealed that the P-glycoprotein molecule encoded by this mutant MDR1-G185V possessed an asparagine residue (rather than the wild-type isoleucine residue) at position 186, and was thus termed MDR1-I186N.

EXAMPLE 2

Isolation of Mutant P-glycoproteins by Array Selection

Figure 2:
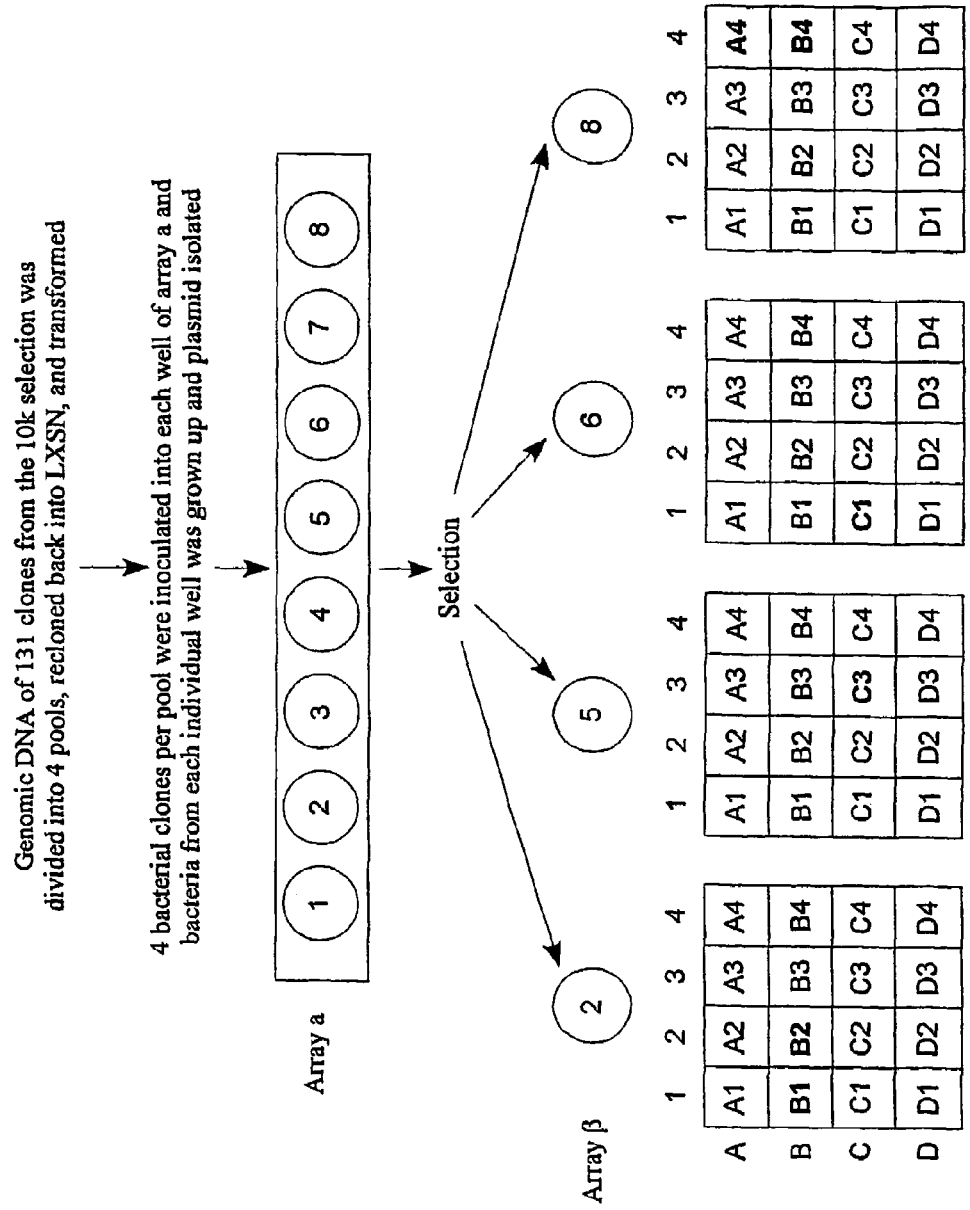
FIG. 2 illustrates the array selection scheme that was used to isolate P-glycoprotein mutants conferring etoposide hyper-resistance.

An array selection strategy was employed to isolate additional MDR1 mutants conferring hyper-resistance to etoposide from the cells transduced with Mut II and selected in 10 μg/mL etoposide, as described in Example 1 (this selection scheme is shown in FIG. 1C and in FIG. 2). The 131 clonal lines from Example 1 were divided into four pools. MDR1 cDNA was recovered by PCR from each of the four pools, recloned back into LXSN, and used to transform bacterial cells to generate four MDR1 mutant libraries. These libraries were plated; individual bacterial colonies were picked and tested by array analysis. For this analysis, each well of a 96-well plate was seeded with four randomly selected colonies from each MDR1 mutant library (for a total of 16 colonies per well), and 8 wells, comprising a total of 128 clones (array α), were tested. Plasmid was recovered from bacteria grown in each well (a 16-clone group) and used to transduce NIH 3T3 cells, and the transduced NIH 3T3 cells were selected in 2 μg/ml etoposide. The cDNA from each of the 16-clone groups that showed survival (groups 2, 5, 6 and 8) was then put into array β. The groups were subdivided into eight overlapping pools, each containing four mutant MDR1 cDNA (FIG. 2; pools A-D and pools 1-4). Each pool was then transduced into NIH 3T3 cells that were then tested for survival in 2 μg/mL etoposide. The shaded boxes in FIG. 2 denote pools that showed survival. The boldfaced numbers in FIG. 2 indicate individual mutant MDR1 cDNA that confer hyper-resistance to etoposide. Six mutants that confer increased etoposide resistance relative to parental MDR1-G185V cDNA were identified in the array selection.

These mutants, designated as 2-B1, 2-B2, 5-C3, 6-C1, 8-A4, and 8-B4were sequenced in both directions. The mutations that were identified in the MDR1-G185V mutants by sequence analysis are shown in Table I. Additional mutations, which were either silent or very conservative, were also found in most of the MDR1-G185V mutants. Four non-conservative mutations were also identified in the MDR1-G185V mutants, but these mutations, when introduced into the MDR1 cDNA as described in Example 3, conferred no greater etoposide resistance than parental MDR1-G185V cDNA.

Four of the mutants were found to have mutations that resulted in amino acid substitutions in the transmembrane (TM) domains (FIGS. 3A-G and Table I). A mutation in the 8-A4 mutant was found to generate a P-glycoprotein molecule having a phenylalanine residue (rather than the wild-type leucine residue) at position 56, which is located in TM1. Three mutations within close proximity of each other in the 5-C3 mutant were found to generate a P-glycoprotein having a phenylalanine residue (rather than the wild-type isoleucine residue) at position 190 and a phenylalanine (rather than the wild-type methionine residue) at position 197, both residues of which are located in TM3. Two mutations in the 2-B2 mutant were found to generate a P-glycoprotein having a tryptophan (rather than the wild-type glycine) at position 763, which is located in TM8. Finally, a mutation in the 2B-1 mutant was found to generate a P-glycoprotein having a glutamic acid (rather than the wild-type glycine) at position 844, which is located in TM9.

Two of the mutants were found to have mutations that resulted in amino acid substitutions in the linker region (FIGS. 3A-G and Table I). Two mutations in the 6-C1 mutant were found to generate a P-glycoprotein molecule having lysine residues (rather than the wild-type glutamic acid) at positions 634 and 636. Three mutations in the 8-B4 mutant were found to generate a P-glycoprotein molecule having lysine residues (rather than the wild-type glycine) at positions 643, 647, and 652.

EXAMPLE 3

Construction and Characterization of Mutant P-glycoproteins Having G185V and I186N Substitutions To confirm that the mutation in the MDR1-I186N mutant was indeed responsible for the elevated etoposide resistance observed in NIH 3T3 cells transduced with this mutant, and to investigate how this mutation interacts with the neighboring G185V mutation, wild-type MDR1 and MDR1-G185V EDNA was modified by site-directed mutagenesis (Quick-Change™ mutagenesis kit; Statagene) to introduce the I186N mutation directly into the P-glycoprotein sequence.

Retroviral vectors carrying LXSN (negative control carrying the neomycin/G418 resistance gene), wild-type MDR1, MDR1-G185V, MDR1-I186N, or MDR1-G185V/I186N were individually transduced into NIH 3T3 cells. Populations transduced with MDR1 containing vectors were stained with the P-glycoprotein-specific monoclonal antibody MRK16, and then sorted to obtain cell populations expressing a similar level of P-glycoprotein.

FIGS. 4A through 4E illustrate the effects of the different mutations on drug resistance conferred by MDR1. The G185V substitution (FIG. 4A; open circles) was found to increase etoposide resistance relative to cells transduced with wild-type MDR1 (closed circles). This correlated with the results shown by Safa et al., 1990, ibid. The I186N substitution (closed triangles) was found to increase etoposide resistance to a similar degree as the G185V substitution. However, cells transduced with the MDR1-G185V/I186N construct were found to exhibit a higher level of etoposide resistance than cells transduced with either the MDR1-G185V or MDR1-I186N constructs.

Similar results were obtained when the transduced cells were analyzed for doxorubicin resistance (FIG. 4C). In cells transduced with either the MDR1-G185V or MDR1-I186N constructs, doxorubicin resistance was enhanced relative to cells transduced with wild-type MDR1. In cells transduced with the MDR1-G185V/I186N construct, an even higher level of doxorubicin resistance was observed.

While the I186N substitution, like the G185V substitution, was found to increase colchicine resistance relative to cells transduced with wild-type MDR1, the G185V substitution (which was originally identified in colchicine-selected cells) was found to confer an even higher level of colchicine resistance (FIG. 4B). However, in contrast to the observations made with respect to etoposide and doxorubicin resistance, cells transduced with the MDR1-G185V/I186N construct exhibited a level of resistance that was indistinguishable from that obtained for cells transduced with the MDR1-G185V construct.

A major functional difference was observed in the resistance conferred by the MDR1 mutants to vinblastine (FIG. 4D) and taxol (FIG. 4E). In agreement with previous reports (Choi et al., 1988, ibid.; Safa et al., 1990, ibid.), the G185V substitution was found to decrease resistance levels to both of these drugs relative to cells transduced with wild-type MDR1. In contrast, the I186N substitution was found to increase resistance to both of these drugs relative to cells transduced with wild-type MDR1. In cells transduced with the MDR1-G185V/I186N construct, the opposite effects of the I186N and G185V substitutions appear to balance out, and therefore, the level of vinblastine and taxol resistance are similar to that observed in cells transduced with wild-type MDR1.

These results indicate that the I186N substitution alone (like the G185V substitution) can confer increased resistance to etoposide and doxorubicin, and that the I186N substitution, when present in combination with the G185V substitution can augment the effect of the latter substitution by conferring an even higher level of etoposide and doxorubicin resistance. These results suggest that a mutant human P-glycoprotein having only a single substitution (e.g., an individual lysine substitution at position 634), similarly to the mutant P-glycoproteins described herein that have multiple substitutions (e.g., lysine substitutions at positions 634 and 636 in the 6-C1 mutant), can confer increased resistance to certain chemotherapeutic drugs compared to wild-type P-glycoprotein or P-glycoprotein having a glycine to valine substitution at position 185.

EXAMPLE 4

Construction and Characterization of Mutant P-glycoproteins 2-B1, 2-B2, 5-C3, 6-C1, 8-A4, and 8-B4

To investigate the mutants 6-C1 and 8-B4 disclosed in Example 2 above, which are located in the linker region separating the two homologous, membrane-spanning domains, MDR1-G185V cDNA was modified by site-directed mutagenesis to create a mutant construct termed LMDR1-G185V-EK2 (wherein "EK2" denoted that two glutamic acid to lysine substitutions had been introduced, at positions 634 and 636) and a mutant construct termed LMDR1-G185V-EK3 construct (wherein "EK3" denoted that three glutamic acid to lysine substitutions had been introduced, at positions 643, 647, and 652). In addition, to test whether an even greater change in the charge of the linker region would yield an even higher level of etoposide resistance, a third construct was created in which the amino acid substitutions of both the 6-C1 and 8-B4 mutants were introduced. This construct was designated LMDR1-G185V-EK5 ("EK5" denoting that glutamic acid to lysine substitutions had been introduced at positions 634, 636, 643, 647 and 652).

NIH 3T3 cells were transduced with the LMDR1-G185V, LMDR1-G185V-EK2, LMDR1-G185V-EK3, or LMDR1-G185V-EK5 constructs, and the transduced cells were then sorted by FACS to generate pure populations of P-glycoprotein positive cells having similar levels of P-glycoprotein. Following sorting, the cell populations were analyzed for their drug resistance. The results of this analysis are shown in FIGS. 5A through 5C. Cells transduced with the LMDR1-G185V-EK2 and LMDR1-G185V-EK3 constructs showed a 1.4 and 1.6-fold increase in etoposide resistance relative to the LMDR1-G185V construct (FIG. 5A; Table II). The level of etoposide resistance obtained in cells transduced with the LMDR1-G185V-EK5 construct, however, indicated that the effect of the double and triple lysine mutants was not additive.

The introduction of the glutamic acid to lysine substitutions in the LMDR1-G185V-EK2 and LMDR1-G185V-EK3 constructs was also found to increase doxorubicin resistance relative to the LMDR1-G185V construct (FIG. 5B). As indicated in Table II, the resistance of the double lysine mutant showed an almost two-fold increase in doxorubicin resistance, while the triple lysine mutant showed nearly a four-fold increase in doxorubicin resistance. As with etoposide resistance, the effect of the double and triple lysine mutants was not additive. This lack of additivity suggests that the increase in drug resistance is likely to be conferred by any combination of one or more glutamic acid to lysine mutations in the linker region, rather than only by the specific EK2 and EK3 combinations tested here.

In contrast to the results obtained for etoposide and doxorubicin, introduction of the glutamic acid to lysine substitutions in the LMDR1-G185V-EK2 and LMDR1-G185V-EK3 constructs was found to decrease colchicine resistance relative to the LMDR1-G185V construct (FIG. 5C). In addition, cells transduced with the LMDR1-G185V-EK5 construct exhibited the greatest decrease in colchicine resistance (Table II). The multiple glutamic acid to lysine substitutions did not seem to affect taxol and vinblastine resistance (Table II).

To investigate the mutants 8-A4, 5-C3, 2-B2, and 2-B1, having mutations in one of the transmembrane domains, MDR1-G185V cDNA was modified by site-directed mutagenesis to create the following constructs: LMDR1-G185V-L56F (leucine to phenylalanine mutation at residue 56), LMDR1-G185V-I190F/M197F (isoleucine to phenylalanine mutation at amino acid residue 190 and methionine to phenylalanine mutation at residue 197), LMDR1-G185V-G763W (glycine to tryptophan mutation at residue 763), and LMDR1-G185V-G844Q (glycine to glutamine mutation at residue 844). NIH 3T3 cells were transduced with either the LMDR1-G185V construct or one of the transmembrane mutant constructs, and the transduced cells were then sorted by FACS to generate pure populations of P-glycoprotein positive cells having similar levels of P-glycoprotein. Following sorting, the cell populations were analyzed for their drug resistance.

Figure 6:
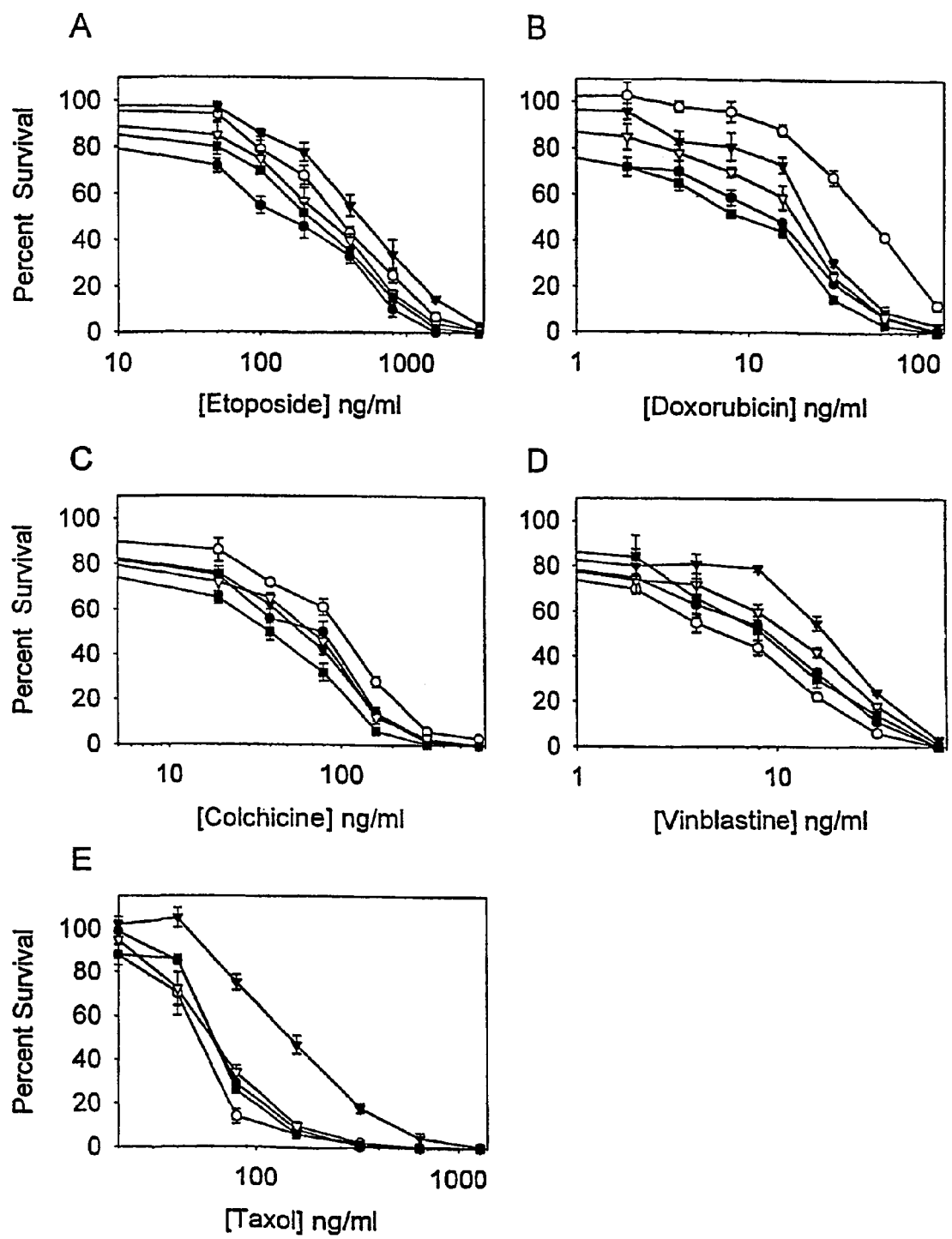
FIGS. 6A through 6E illustrate the results of clonogenic assays for resistance to etoposide (panel A), doxorubicin (panel B), colchicine (panel C), vinblastine (panel D), and taxol (panel E) for NIH 3T3 cells transduced with LMDR1-G185V (closed circles), LMDR1-G185V-L56F (open circles), LMDR1-G185V-I190F/M197F (closed triangles), LMDR1-G185V-G763W (open triangles), or LMDR1-G185V-G844Q (closed squares).

All of the mutants conferred increased resistance to etoposide with the I190F/M197F mutant yielding the greatest resistance (FIG. 6A; Table II). While only the L56F mutant conferred increased colchicine resistance, the G844Q mutant was found to exhibit decreased colchicine resistance (FIG. 6C; Table II). With the exception of the G844Q mutant, each of the mutants showed an increased doxorubicin resistance relative to the LMDR1-G185V construct (FIG. 6B). While the L56F mutant conferred very strong resistance to doxorubicin, the I190F/M197F and G763W mutants only conferred moderate increases in doxorubicin resistance (Table II). Although the I190F/M197F and G763W mutants were both found to confer increased vinblastine resistance (the latter mutant showing only a moderate increase in vinblastine resistance), the L56F mutant exhibited decreased vinblastine resistance (FIG. 6D; Table II). While the L56F mutant also exhibited decreased taxol resistance, the I190F/M196F mutant showed a significant increase in taxol resistance, and the G763W and G844Q mutants appeared to have no effect on taxol resistance (FIG. 6E; Table II).

Since the I186N substitution was found to increase etoposide resistance even when introduced into wild-type MDR1 alone (i.e., not in tandem with the G185V substitution), it is likely that the substitutions described above would also confer increased resistance to etoposide when introduced into wild-type MDR1 alone or in combinations.

It should be understood that the foregoing disclosure emphasizes certain specific embodiments of the invention and that all modifications or alternatives equivalent thereto are within the spirit and scope of the invention as set forth in the appended claims.

We claim:

1. An isolated nucleic acid molecule comprising a nucleotide sequence encoding human P-glycoprotein and having an asparagine residue at position 186, a phenylalanine residue at position 56, a phenylalanine residue at positions 190 and 197, a tryptophan residue at position 763, a glutamic acid residue at position 844, a lysine residue at positions 634 and 636, a lysine residue at positions 643, 647, and 652, a lysine residue at positions 634, 636, 643, 647, and 652, a phenylalanine residue at position 190, a phenylalanine residue at position 197, a lysine residue at position 634, a lysine residue at position 636, a lysine residue at position 643, a lysine residue at position 647, or a lysine residue at position 652 of the human P-glycoprotein amino acid sequence.

2. An isolated nucleic acid molecule according to claim 1, comprising a nucleotide sequence encoding human P-glycoprotein and having a phenylalanine residue at position 56.

3. An isolated nucleic acid molecule according to claim 1, comprising a nucleotide sequence encoding human P-glycoprotein and having a phenylalanine residue at positions 190 and 197.

4. An isolated nucleic acid molecule according to claim 1, comprising a nucleotide sequence encoding human P-glycoprotein and having a tryptophan residue at position 763.

5. An isolated nucleic acid molecule according to claim 1, comprising a nucleotide sequence encoding human P-glycoprotein and having a glutamic acid residue at position 844.

6. An isolated nucleic acid molecule according to claim 1, comprising a nucleotide sequence encoding human P-glycoprotein and having a lysine residue at positions 634 and 636.

7. An isolated nucleic acid molecule according to claim 1, comprising a nucleotide sequence encoding human P-glycoprotein and having a lysine residue at positions 643, 647, and 652.

8. An isolated nucleic acid molecule according to claim 1, comprising a nucleotide sequence encoding human P-glycoprotein and having a lysine residue at positions 634, 636, 643, 647, and 652.

9. An isolated nucleic acid molecule according to claim 1, comprising a nucleotide sequence encoding human P-glycoprotein and having a phenylalanine residue at position 190.

10. An isolated nucleic acid molecule according to claim 1, comprising a nucleotide sequence encoding human P-glycoprotein and having a phenylalanine residue at position 197.

11. An isolated nucleic acid molecule according to claim 1, comprising a nucleotide sequence encoding human P-glycoprotein and having a lysine residue at position 634.

12. An isolated nucleic acid molecule according to claim 1, comprising a nucleotide sequence encoding human P-glycoprotein and having a lysine residue at position 636.

13. An isolated nucleic acid molecule according to claim 1, comprising a nucleotide sequence encoding human P-glycoprotein and having a lysine residue at position 643.

14. An isolated nucleic acid molecule according to claim 1, comprising a nucleotide sequence encoding human P-glycoprotein and having a lysine residue at position 647.

15. An isolated nucleic acid molecule according to claim 1, comprising a nucleotide sequence encoding human P-glycoprotein and having a lysine residue at position 652.

16. An isolated nucleic acid molecule according to claim 1, comprising a nucleotide sequence encoding human P-glycoprotein and having at least one amino acid substitution selected from the group consisting of
   (a) an asparagine residue at position 186;
   (b) a phenylalanine residue at position 56;
   (c) a phenylalanine residue at positions 190 and 197;
   (d) a tryptophan residue at position 763;
   (e) a glutamic acid residue at position 844;
   (f) a lysine residue at positions 634 and 636; and
   (g) a lysine residue at positions 643, 647, and 652.

17. An isolated nucleic acid molecule according to claim 1, comprising a nucleotide sequence encoding human P-glycoprotein and having at least one amino acid substitution selected from the group consisting of:
   (a) an asparagine residue at position 186;
   (b) a phenylalanine residue at position 56;
   (c) a phenylalanine residue at position 190;
   (d) a phenylalanine residue at position 197;
   (e) a tryptophan residue at position 763;
   (f) a glutamic acid residue at position 844;
   (g) a lysine residue at position 634;
   (h) a lysine residue at position 636;
   (i) a lysine residue at position 643;
   (j) a lysine residue at position 647; and
   (k) a lysine residue at position 652.

18. An isolated nucleic acid molecule according to claim 1 comprising a nucleotide sequence encoding human P-glycoprotein and having an asparagine residue at position 186.

19. An isolated nucleic acid molecule comprising a nucleotide sequence encoding a polypeptide as set forth in any of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

20. An isolated nucleic acid molecule according to claim 1, comprising a nucleotide sequence encoding a polypeptide as set forth in SEQ ID NO: 2 and having at least one amino acid substitution selected from the group consisting of:
   (a) an asparagine residue at position 186;
   (b) a phenylalanine residue at position 56;
   (c) a phenylalanine residue at positions 190 and 197;
   (d) a tryptophan residue at position 763;
   (e) a glutamic acid residue at position 844;
   (f) a lysine residue at positions 634 and 636; and
   (g) a lysine residue at positions 643, 647, and 652.

21. An isolated nucleic acid molecule according to claim 1, comprising a nucleotide sequence encoding a polypeptide as set forth in SEQ ID NO: 2 having at least one amino acid substitution selected from the group consisting of:
   (a) an asparagine residue at position 186;
   (b) a phenylalanine residue at position 56;
   (c) a phenylalanine residue at position 190;
   (d) a phenylalanine residue at position 197;
   (e) a tryptophan residue at position 763;
   (f) a glutamic acid residue at position 844;
   (g) a lysine residue at position 634;
   (h) a lysine residue at position 636;
   (i) a lysine residue at position 643;
   (j) a lysine residue at position 647; and
   (k) a lysine residue at position 652.

22. The isolated nucleic acid molecule of any one of claims 1-21 having a valine at position 185.

23. A recombinant expression construct comprising the nucleic acid molecule of claim 22.

24. A recombinant expression construct comprising the nucleic acid molecule of any one of claims 1-21.

25. A mammalian cell culture comprising a recombinant expression construct according to claim 24.

26. An isolated human P-glycoprotein molecule having an asparagine residue at position 186, a phenylalanine residue at position 56, a phenylalanine residue at positions 190 and 197, a tryptophan residue at position 763, a glutamic acid residue at position 844, a lysine residue at positions 634 and 636, a lysine residue at positions 643, 647, and 652, a lysine residue at positions 634, 636, 643, 647, and 652, a phenylalanine residue at position 190, a phenylalanine residue at position 197, a lysine residue at position 634, a lysine residue at position 636, a lysine residue at position 643, a lysine residue at position 647, or a lysine residue at position 652 of the human P-glycoprotein amino acid sequence.

27. An isolated human P-glycoprotein molecule according to claim 26, having a phenylalanine residue at position 56.

28. An isolated human P-glycoprotein molecule according to claim 26, having a phenylalanine residue at positions 190 and 197.

29. An isolated human P-glycoprotein molecule according to claim 26, having a tryptophan residue at position 763.

30. An isolated human P-glycoprotein molecule according to claim 26, having a glutamic acid residue at position 844.

31. An isolated human P-glycoprotein molecule according to claim 26, having a lysine residue at positions 634 and 636.

32. An isolated human P-glycoprotein molecule according to claim 26, having a lysine residue at positions 643, 647, and 652.

33. An isolated human P-glycoprotein molecule according to claim 26, having a lysine residue at positions 634, 636, 643, 647, and 652.

34. An isolated human P-glycoprotein molecule according to claim 26, having a phenylalanine residue at position 190.

35. An isolated human P-glycoprotein molecule according to claim 26, having a phenylalanine residue at position 197.

36. An isolated human P-glycoprotein molecule according to claim 26, having a lysine residue at position 634.

37. An isolated human P-glycoprotein molecule according to claim 26, having a lysine residue at position 636.

38. An isolated human P-glycoprotein molecule according to claim 26, having a lysine residue at position 643.

39. An isolated human P-glycoprotein molecule according to claim 26, having a lysine residue at position 647.

40. An isolated human P-glycoprotein molecule according to claim 26, having a lysine residue at positions 652.

41. An isolated human P-glycoprotein molecule according to claim 26, having at least one amino acid substitution selected from the group consisting of:
   (a) an asparagine residue at position 186;
   (b) a phenylalanine residue at position 56;
   (c) a phenylalanine residue at positions 190 and 197;
   (d) a tryptophan residue at position 763;
   (e) a glutamic acid residue at position 844;

(f) a lysine residue at positions 634 and 636; and
(g) a lysine residue at positions 643, 647, and 652.

42. An isolated human P-glycoprotein molecule according to claim 26, having at least one amino acid substitution selected from the group consisting of:
    (a) an asparagine residue at position 186;
    (b) a phenylalanine residue at position 56;
    (c) a phenylalanine residue at position 190;
    (d) a phenylalanine residue at position 197;
    (e) a tryptophan residue at position 763;
    (f) a glutamic acid residue at position 844;
    (g) a lysine residue at position 634;
    (h) a lysine residue at position 636;
    (i) a lysine residue at position 643;
    (j) a lysine residue at position 647; and
    (k) a lysine residue at position 652.

43. An isolated polypeptide according to claim 26 having an asparagine residue at position 186.

44. An isolated polypeptide according to claim 26 and as set forth in SEQ ID NO: 2 having at least one amino acid substitution selected from the group consisting of:
    (a) an asparagine residue at position 186;
    (b) a phenylalanine residue at position 56;
    (c) a phenylalanine residue at positions 190 and 197;
    (d) a tryptophan residue at position 763;
    (e) a glutamic acid residue at position 844;
    (f) a lysine residue at positions 634 and 636; and
    (g) a lysine residue at positions 643, 647, and 652.

45. An isolated polypeptide according to claim 26 and as set forth in SEQ ID NO: 2 having at least one amino acid substitution selected from the group consisting of:
    (a) an asparagine residue at position 186;
    (b) a phenylalanine residue at position 56;
    (c) a phenylalanine residue at position 190;
    (d) a phenylalanine residue at position 197;
    (e) a tryptophan residue at position 763;
    (f) a glutarnic acid residue at position 844;
    (g) a lysine residue at position 634;
    (h) a lysine residue at position 636;
    (i) a lysine residue at position 643;
    (j) a lysine residue at position 647; and
    (k) a lysine residue at position 652.

46. The isolated polypeptide of any one of claims 26-45 having a valine at position 185.

47. An isolated polypeptide as set forth in any of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

48. A method for determining whether a human tumor sample comprises tumor cells expressing a mutant P-glycoprotein, wherein the method comprises the steps of:
    (a) hybridizing an mRNA or cDNA sample from said tumor cells comprising the human tumor sample with a nucleic acid probe specific for the nucleotide sequence of said mutant P-glycoprotein overnight at 42° C. in a hybridization buffer comprising 6× SSC, 2× Denhardt's solution and 0.25% SDS;
    (b) washing hybridized mRNA or cDNA in an excess volume of 6× SSC and 0.05% SDS sequentially at temperatures increasing from room temperature to 63° C. for a time sufficient to remove a non-specific hybridization;
wherein the said mutant P-glycoprotein comprises at least one amino acid substitution selected from the group consisting of:
    (a) an asparagine residue at position 186;
    (b) a phenylalanine residue at position 56;
    (c) a phenylalanine residue at positions 190 and 197;
    (d) a tryptophan residue at position 763;
    (e) a glutamic acid residue at position 844;
    (f) a lysine residue at positions 634 and 636; and
    (g) a lysine residue at positions 643, 647, and 652,
    (i) a lysine residue at positions 634, 636, 643, 647, and 652;
    (k) a phenylalanine residue at position 190;
    (l) a phenylalanine residue at position 197;
    (m) a lysine residue at position 634;
    (n) a lysine residue at position 636;
    (o) a lysine residue at position 643;
    (p) a lysine residue at position 647; and
    (q) a lysine residue at position 652;
and, wherein said nucleic acid probe comprises a nucleotide sequence encoding a mutant P-glycoprotein or fragment thereof having at least one mutated amino acid residue specific to said mutant P-glycoprotein.

49. A method for determining whether a human tumor sample comprises tumor cells expressing a mutant P-glycoprotein, the method comprising the steps of amplifying in vitro a nucleic acid fragment comprising an mRNA or cDNA sample from said tumor cells, wherein said nucleic acid fragment comprises a nucleotide sequence encoding a mutant P-glycoprotein or fragment thereof having at least one mutated amino acid residue selected from the group consisting of:
    (a) an asparagine residue at position 186;
    (b) a phenylalanine residue at position 56;
    (c) a phenylalanine residue at positions 190 and 197;
    (d) a tryptophan residue at position 763;
    (e) a glutamic acid residue at position 844;
    (f) a lysine residue at positions 634 and 636; and
    (g) a lysine residue at positions 643, 647, and 652,
    (j) a lysine residue at positions 634, 636, 643, 647, and 652;
    (k) a phenylalanine residue at position 190;
    (l) a phenylalanine residue at position 197;
    (m) a lysine residue at position 634;
    (n) a lysine residue at position 636;
    (o) a lysine residue at position 643;
    (p) a lysine residue at position 647; and
    (q) a lysine residue at position 652.

* * * * *

SEQUENCE LISTING

<160> NUMBER OF SEQ ID NOS: 18

<210> SEQ ID NO 1
<211> LENGTH: 4646
<212> TYPE: DNA
<213> ORGANISM: Homo sapiens
<220> FEATURE:
<221> NAME/KEY: CDS
<222> LOCATION: (425)..(4264)

<400> SEQUENCE: 1

```
cctactctat tcagatattc tccagattcc taaagattag agatcatttc tcattctcct      60
aggagtactc acttcaggaa gcaaccagat aaaagagagg tgcaacggaa gccagaacat     120
tcctcctgga aattcaacct gtttcgcagt ttctcgagga atcagcattc agtcaatccg     180
ggccgggagc agtcatctgt ggtgaggctg attggctggg caggaacagc gccggggcgt     240
gggctgagca cagcgcttcg ctctctttgc cacaggaagc ctgagctcat tcgagtagcg     300
gctcttccaa gctcaaagaa gcagaggccg ctgttcgttt cctttaggtc tttccactaa     360
agtcggagta tcttcttcca agatttcacg tcttggtggc cgttccaagg agcgcgaggt     420 cggg atg gat ctt gaa ggg gac cgc aat gga gga gca aag aag aag aac     469
     Met Asp Leu Glu Gly Asp Arg Asn Gly Gly Ala Lys Lys Lys Asn
       1               5                  10                  15 ttt ttt aaa ctg aac aat aaa agt gaa aaa gat aag aag gaa aag aaa     517
```

|  |  |
|---|---|
| Phe Phe Lys Leu Asn Asn Lys Ser Glu Lys Asp Lys Lys Glu Lys Lys<br>                     20                        25                    30 |  |
| cca act gtc agt gta ttt tca atg ttt cgc tat tca aat tgg ctt gac<br>Pro Thr Val Ser Val Phe Ser Met Phe Arg Tyr Ser Asn Trp Leu Asp<br>              35                    40                    45 | 565 |
| aag ttg tat atg gtg gtg gga act ttg gct gcc atc atc cat ggg gct<br>Lys Leu Tyr Met Val Val Gly Thr Leu Ala Ala Ile Ile His Gly Ala<br>              50                    55                    60 | 613 |
| gga ctt cct ctc atg atg ctg gtg ttt gga gaa atg aca gat atc ttt<br>Gly Leu Pro Leu Met Met Leu Val Phe Gly Glu Met Thr Asp Ile Phe<br>65                    70                    75 | 661 |
| gca aat gca gga aat tta gaa gat ctg atg tca aac atc act aat aga<br>Ala Asn Ala Gly Asn Leu Glu Asp Leu Met Ser Asn Ile Thr Asn Arg<br>80                    85                    90                    95 | 709 |
| agt gat atc aat gat aca ggg ttc ttc atg aat ctg gag gaa gac atg<br>Ser Asp Ile Asn Asp Thr Gly Phe Phe Met Asn Leu Glu Glu Asp Met<br>                     100                   105                   110 | 757 |
| acc agg tat gcc tat tat tac agt gga att ggt gct ggg gtg ctg gtt<br>Thr Arg Tyr Ala Tyr Tyr Tyr Ser Gly Ile Gly Ala Gly Val Leu Val<br>               115                   120                   125 | 805 |
| gct gct tac att cag gtt tca ttt tgg tgc ctg gca gct gga aga caa<br>Ala Ala Tyr Ile Gln Val Ser Phe Trp Cys Leu Ala Ala Gly Arg Gln<br>               130                   135                   140 | 853 |
| ata cac aaa att aga aaa cag ttt ttt cat gct ata atg cga cag gag<br>Ile His Lys Ile Arg Lys Gln Phe Phe His Ala Ile Met Arg Gln Glu<br>             145                   150                   155 | 901 |
| ata ggc tgg ttt gat gtg cac gat gtt ggg gag ctt aac acc cga ctt<br>Ile Gly Trp Phe Asp Val His Asp Val Gly Glu Leu Asn Thr Arg Leu<br>160                     165                   170                   175 | 949 |
| aca gat gat gtc tct aag att aat gaa gga att ggt gac aaa att gga<br>Thr Asp Asp Val Ser Lys Ile Asn Glu Gly Ile Gly Asp Lys Ile Gly<br>                     180                   185                   190 | 997 |
| atg ttc ttt cag tca atg gca aca ttt ttc act ggg ttt ata gta gga<br>Met Phe Phe Gln Ser Met Ala Thr Phe Phe Thr Gly Phe Ile Val Gly<br>               195                   200                   205 | 1045 |
| ttt aca cgt ggt tgg aag cta acc ctt gtg att ttg gcc atc agt cct<br>Phe Thr Arg Gly Trp Lys Leu Thr Leu Val Ile Leu Ala Ile Ser Pro<br>             210                   215                   220 | 1093 |
| gtt ctt gga ctg tca gct gct gtc tgg gca aag ata cta tct tca ttt<br>Val Leu Gly Leu Ser Ala Ala Val Trp Ala Lys Ile Leu Ser Ser Phe<br>225                     230                   235 | 1141 |
| act gat aaa gaa ctc tta gcg tat gca aaa gct gga gca gta gct gaa<br>Thr Asp Lys Glu Leu Leu Ala Tyr Ala Lys Ala Gly Ala Val Ala Glu<br>240                     245                   250                   255 | 1189 |
| gag gtc ttg gca gca att aga act gtg att gca ttt gga gga caa aag<br>Glu Val Leu Ala Ala Ile Arg Thr Val Ile Ala Phe Gly Gly Gln Lys<br>             260                   265                   270 | 1237 |
| aaa gaa ctt gaa agg tac aac aaa aat tta gaa gaa gct aaa aga att<br>Lys Glu Leu Glu Arg Tyr Asn Lys Asn Leu Glu Glu Ala Lys Arg Ile<br>             275                   280                   285 | 1285 |
| ggg ata aag aaa gct att aca gcc aat att tct ata ggt gct gct ttc<br>Gly Ile Lys Lys Ala Ile Thr Ala Asn Ile Ser Ile Gly Ala Ala Phe<br>             290                   295                   300 | 1333 |
| ctg ctg atc tat gca tct tat gct ctg gcc ttc tgg tat ggg acc acc<br>Leu Leu Ile Tyr Ala Ser Tyr Ala Leu Ala Phe Trp Tyr Gly Thr Thr<br>             305                   310                   315 | 1381 |
| ttg gtc ctc tca ggg gaa tat tct att gga caa gta ctc act gta ttc<br>Leu Val Leu Ser Gly Glu Tyr Ser Ile Gly Gln Val Leu Thr Val Phe<br>320                     325                   330                   335 | 1429 |

```
                                                              -continued ttt tct gta tta att ggg gct ttt agt gtt gga cag gca tct cca agc        1477
Phe Ser Val Leu Ile Gly Ala Phe Ser Val Gly Gln Ala Ser Pro Ser
            340                 345                 350 att gaa gca ttt gca aat gca aga gga gca gct tat gaa atc ttc aag        1525
Ile Glu Ala Phe Ala Asn Ala Arg Gly Ala Ala Tyr Glu Ile Phe Lys
355                 360                 365 ata att gat aat aag cca agt att gac agc tat tcg aag agt ggg cac        1573
Ile Ile Asp Asn Lys Pro Ser Ile Asp Ser Tyr Ser Lys Ser Gly His
        370                 375                 380 aaa cca gat aat att aag gga aat ttg gaa ttc aga aat gtt cac ttc        1621
Lys Pro Asp Asn Ile Lys Gly Asn Leu Glu Phe Arg Asn Val His Phe
385                 390                 395 agt tac cca tct cga aaa gaa gtt aag atc ttg aag ggc ctg aac ctg        1669
Ser Tyr Pro Ser Arg Lys Glu Val Lys Ile Leu Lys Gly Leu Asn Leu
400                 405                 410                 415 aag gtg cag agt ggg cag acg gtg gcc ctg gtt gga aac agt ggc tgt        1717
Lys Val Gln Ser Gly Gln Thr Val Ala Leu Val Gly Asn Ser Gly Cys
            420                 425                 430 ggg aag agc aca aca gtc cag ctg atg cag agg ctc tat gac ccc aca        1765
Gly Lys Ser Thr Thr Val Gln Leu Met Gln Arg Leu Tyr Asp Pro Thr
                435                 440                 445 gag ggg atg gtc agt gtt gat gga cag gat att agg acc ata aat gta        1813
Glu Gly Met Val Ser Val Asp Gly Gln Asp Ile Arg Thr Ile Asn Val
            450                 455                 460 agg ttt cta cgg gaa atc att ggt gtg gtg agt cag gaa cct gta ttg        1861
Arg Phe Leu Arg Glu Ile Ile Gly Val Val Ser Gln Glu Pro Val Leu
465                 470                 475 ttt gcc acc acg ata gct gaa aac att cgc tat ggc cgt gaa aat gtc        1909
Phe Ala Thr Thr Ile Ala Glu Asn Ile Arg Tyr Gly Arg Glu Asn Val
480                 485                 490                 495 acc atg gat gag att gag aaa gct gtc aag gaa gcc aat gcc tat gac        1957
Thr Met Asp Glu Ile Glu Lys Ala Val Lys Glu Ala Asn Ala Tyr Asp
            500                 505                 510 ttt atc atg aaa ctg cct cat aaa ttt gac acc ctg gtt gga gag aga        2005
Phe Ile Met Lys Leu Pro His Lys Phe Asp Thr Leu Val Gly Glu Arg
                515                 520                 525 ggg gcc cag ttg agt ggt ggg cag aag cag agg atc gcc att gca cgt        2053
Gly Ala Gln Leu Ser Gly Gly Gln Lys Gln Arg Ile Ala Ile Ala Arg
            530                 535                 540 gcc ctg gtt cgc aac ccc aag atc ctc ctg ctg gat gag gcc acg tca        2101
Ala Leu Val Arg Asn Pro Lys Ile Leu Leu Leu Asp Glu Ala Thr Ser
545                 550                 555 gcc ttg gac aca gaa agc gaa gca gtg gtt cag gtg gct ctg gat aag        2149
Ala Leu Asp Thr Glu Ser Glu Ala Val Val Gln Val Ala Leu Asp Lys
560                 565                 570                 575 gcc aga aaa ggt cgg acc acc att gtg ata gct cat cgt ttg tct aca        2197
Ala Arg Lys Gly Arg Thr Thr Ile Val Ile Ala His Arg Leu Ser Thr
            580                 585                 590 gtt cgt aat gct gac gtc atc gct ggt ttc gat gat gga gtc att gtg        2245
Val Arg Asn Ala Asp Val Ile Ala Gly Phe Asp Asp Gly Val Ile Val
                595                 600                 605 gag aaa gga aat cat gat gaa ctc atg aaa gag aaa ggc att tac ttc        2293
Glu Lys Gly Asn His Asp Glu Leu Met Lys Glu Lys Gly Ile Tyr Phe
            610                 615                 620 aaa ctt gtc aca atg cag aca gca gga aat gaa gtt gaa tta gaa aat        2341
Lys Leu Val Thr Met Gln Thr Ala Gly Asn Glu Val Glu Leu Glu Asn
625                 630                 635 gca gct gat gaa tcc aaa agt gaa att gat gcc ttg gaa atg tct tca        2389
Ala Ala Asp Glu Ser Lys Ser Glu Ile Asp Ala Leu Glu Met Ser Ser
640                 645                 650                 655
```

```
aat gat tca aga tcc agt cta ata aga aaa aga tca act cgt agg agt    2437
Asn Asp Ser Arg Ser Ser Leu Ile Arg Lys Arg Ser Thr Arg Arg Ser
            660                 665                 670 gtc cgt gga tca caa gcc caa gac aga aag ctt agt acc aaa gag gct    2485
Val Arg Gly Ser Gln Ala Gln Asp Arg Lys Leu Ser Thr Lys Glu Ala
        675                 680                 685 ctg gat gaa agt ata cct cca gtt tcc ttt tgg agg att atg aag cta    2533
Leu Asp Glu Ser Ile Pro Pro Val Ser Phe Trp Arg Ile Met Lys Leu
                690                 695                 700 aat tta act gaa tgg cct tat ttt gtt gtt ggt gta ttt tgt gcc att    2581
Asn Leu Thr Glu Trp Pro Tyr Phe Val Val Gly Val Phe Cys Ala Ile
            705                 710                 715 ata aat gga ggc ctg caa cca gca ttt gca ata ata ttt tca aag att    2629
Ile Asn Gly Gly Leu Gln Pro Ala Phe Ala Ile Ile Phe Ser Lys Ile
720                 725                 730                 735 ata ggg gtt ttt aca aga att gat gat cct gaa aca aaa cga cag aat    2677
Ile Gly Val Phe Thr Arg Ile Asp Asp Pro Glu Thr Lys Arg Gln Asn
                740                 745                 750 agt aac ttg ttt tca cta ttg ttt cta gcc ctt gga att att tct ttt    2725
Ser Asn Leu Phe Ser Leu Leu Phe Leu Ala Leu Gly Ile Ile Ser Phe
            755                 760                 765 att aca ttt ttc ctt cag ggt ttc aca ttt ggc aaa gct gga gag atc    2773
Ile Thr Phe Phe Leu Gln Gly Phe Thr Phe Gly Lys Ala Gly Glu Ile
770                 775                 780 ctc acc aag cgg ctc cga tac atg gtt ttc cga tcc atg ctc aga cag    2821
Leu Thr Lys Arg Leu Arg Tyr Met Val Phe Arg Ser Met Leu Arg Gln
            785                 790                 795 gat gtg agt tgg ttt gat gac cct aaa aac acc act gga gca ttg act    2869
Asp Val Ser Trp Phe Asp Asp Pro Lys Asn Thr Thr Gly Ala Leu Thr
800                 805                 810                 815 acc agg ctc gcc aat gat gct gct caa gtt aaa ggg gct ata ggt tcc    2917
Thr Arg Leu Ala Asn Asp Ala Ala Gln Val Lys Gly Ala Ile Gly Ser
                820                 825                 830 agg ctt gct gta att acc cag aat ata gca aat ctt ggg aca gga ata    2965
Arg Leu Ala Val Ile Thr Gln Asn Ile Ala Asn Leu Gly Thr Gly Ile
            835                 840                 845 att ata tcc ttc atc tat ggt tgg caa cta aca ctg tta ctc tta gca    3013
Ile Ile Ser Phe Ile Tyr Gly Trp Gln Leu Thr Leu Leu Leu Leu Ala
            850                 855                 860 att gta ccc atc att gca ata gca gga gtt gtt gaa atg aaa atg ttg    3061
Ile Val Pro Ile Ile Ala Ile Ala Gly Val Val Glu Met Lys Met Leu
865                 870                 875 tct gga caa gca ctg aaa gat aag aaa gaa cta gaa ggt gct ggg aag    3109
Ser Gly Gln Ala Leu Lys Asp Lys Lys Glu Leu Glu Gly Ala Gly Lys
880                 885                 890                 895 atc gct act gaa gca ata gaa aac ttc cga acc gtt gtt tct ttg act    3157
Ile Ala Thr Glu Ala Ile Glu Asn Phe Arg Thr Val Val Ser Leu Thr
                900                 905                 910 cag gag cag aag ttt gaa cat atg tat gct cag agt ttg cag gta cca    3205
Gln Glu Gln Lys Phe Glu His Met Tyr Ala Gln Ser Leu Gln Val Pro
            915                 920                 925 tac aga aac tct ttg agg aaa gca cac atc ttt gga att aca ttt tcc    3253
Tyr Arg Asn Ser Leu Arg Lys Ala His Ile Phe Gly Ile Thr Phe Ser
            930                 935                 940 ttc acc cag gca atg atg tat ttt tcc tat gct gga tgt ttc cgg ttt    3301
Phe Thr Gln Ala Met Met Tyr Phe Ser Tyr Ala Gly Cys Phe Arg Phe
945                 950                 955 gga gcc tac ttg gtg gca cat aaa ctc atg agc ttt gag gat gtt ctg    3349
Gly Ala Tyr Leu Val Ala His Lys Leu Met Ser Phe Glu Asp Val Leu
```

-continued

```
                960              965              970              975
tta gta ttt tca gct gtt gtc ttt ggt gcc atg gcc gtg ggg caa gtc         3397
Leu Val Phe Ser Ala Val Val Phe Gly Ala Met Ala Val Gly Gln Val
                980              985              990 agt tca ttt gct cct gac tat gcc aaa gcc aaa ata tca gca gcc cac         3445
Ser Ser Phe Ala Pro Asp Tyr Ala Lys Ala Lys Ile Ser Ala Ala His
        995              1000             1005 atc atc atg atc att gaa aaa acc cct ttg att gac agc tac agc acg         3493
Ile Ile Met Ile Ile Glu Lys Thr Pro Leu Ile Asp Ser Tyr Ser Thr
            1010             1015             1020 gaa ggc cta atg ccg aac aca ttg gaa gga aat gtc aca ttt ggt gaa         3541
Glu Gly Leu Met Pro Asn Thr Leu Glu Gly Asn Val Thr Phe Gly Glu
        1025             1030             1035 gtt gta ttc aac tat ccc acc cga ccg gac atc cca gtg ctt cag gga         3589
Val Val Phe Asn Tyr Pro Thr Arg Pro Asp Ile Pro Val Leu Gln Gly
1040             1045             1050             1055 ctg agc ctg gag gtg aag aag ggc cag acg ctg gct ctg gtg ggc agc         3637
Leu Ser Leu Glu Val Lys Lys Gly Gln Thr Leu Ala Leu Val Gly Ser
                1060             1065             1070 agt ggc tgt ggg aag agc aca gtg gtc cag ctc ctg gag cgg ttc tac         3685
Ser Gly Cys Gly Lys Ser Thr Val Val Gln Leu Leu Glu Arg Phe Tyr
            1075             1080             1085 gac ccc ttg gca ggg aaa gtg ctg ctt gat ggc aaa gaa ata aag cga         3733
Asp Pro Leu Ala Gly Lys Val Leu Leu Asp Gly Lys Glu Ile Lys Arg
        1090             1095             1100 ctg aat gtt cag tgg ctc cga gca cac ctg ggc atc gtg tcc cag gag         3781
Leu Asn Val Gln Trp Leu Arg Ala His Leu Gly Ile Val Ser Gln Glu
        1105             1110             1115 ccc atc ctg ttt gac tgc agc att gct gag aac att gcc tat gga gac         3829
Pro Ile Leu Phe Asp Cys Ser Ile Ala Glu Asn Ile Ala Tyr Gly Asp
1120             1125             1130             1135 aac agc cgg gtg gtg tca cag gaa gag atc gtg agg gca gca aag gag         3877
Asn Ser Arg Val Val Ser Gln Glu Glu Ile Val Arg Ala Ala Lys Glu
                1140             1145             1150 gcc aac ata cat gcc ttc atc gag tca ctg cct aat aaa tat agc act         3925
Ala Asn Ile His Ala Phe Ile Glu Ser Leu Pro Asn Lys Tyr Ser Thr
            1155             1160             1165 aaa gta gga gac aaa gga act cag ctc tct ggt ggc cag aaa caa cgc         3973
Lys Val Gly Asp Lys Gly Thr Gln Leu Ser Gly Gly Gln Lys Gln Arg
        1170             1175             1180 att gcc ata gct cgt gcc ctt gtt aga cag cct cat att ttg ctt ttg         4021
Ile Ala Ile Ala Arg Ala Leu Val Arg Gln Pro His Ile Leu Leu Leu
        1185             1190             1195 gat gaa gcc acg tca gct ctg gat aca gaa agt gaa aag gtt gtc caa         4069
Asp Glu Ala Thr Ser Ala Leu Asp Thr Glu Ser Glu Lys Val Val Gln
1200             1205             1210             1215 gaa gcc ctg gac aaa gcc aga gaa ggc cgc acc tgc att gtg att gct         4117
Glu Ala Leu Asp Lys Ala Arg Glu Gly Arg Thr Cys Ile Val Ile Ala
                1220             1225             1230 cac cgc ctg tcc acc atc cag aat gca gac tta ata gtg gtg ttt cag         4165
His Arg Leu Ser Thr Ile Gln Asn Ala Asp Leu Ile Val Val Phe Gln
            1235             1240             1245 aat ggc aga gtc aag gag cat ggc acg cat cag cag ctg ctg gca cag         4213
Asn Gly Arg Val Lys Glu His Gly Thr His Gln Gln Leu Leu Ala Gln
        1250             1255             1260 aaa ggc atc tat ttt tca atg gtc agt gtc cag gct gga aca aag cgc         4261
Lys Gly Ile Tyr Phe Ser Met Val Ser Val Gln Ala Gly Thr Lys Arg
        1265             1270             1275 cag tgaactctga ctgtatgaga tgttaaatac ttttaatat ttgtttagat              4314
```

Gln
1280 atgacattta ttcaaagtta aaagcaaaca cttacagaat tatgaagagg tatctgttta    4374 acatttcctc agtcaagttc agagtcttca gagacttcgt aattaaagga acagagtgag    4434 agacatcatc aagtggagag aaatcatagt ttaaactgca ttataaattt tataacagaa    4494 ttaaagtaga ttttaaaaga taaaatgtgt aattttgttt atattttccc atttggactg    4554 taactgactg ccttgctaaa agattataga agtagcaaaa agtattgaaa tgtttgcata    4614 aagtgtctat aataaaacta aactttcatg tg    4646

<210> SEQ ID NO 2
<211> LENGTH: 1280
<212> TYPE: PRT
<213> ORGANISM: Homo sapiens

<400> SEQUENCE: 2

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

```
Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Tyr Glu Ile Phe Lys Ile
    355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
                515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
                595                 600                 605

Lys Gly Asn His Asp Glu Leu Met Lys Glu Lys Gly Ile Tyr Phe Lys
                610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
                675                 680                 685

Asp Glu Ser Ile Pro Pro Val Ser Phe Trp Arg Ile Met Lys Leu Asn
                690                 695                 700

Leu Thr Glu Trp Pro Tyr Phe Val Val Gly Val Phe Cys Ala Ile Ile
705                 710                 715                 720
```

```
Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Phe Gly Ala Met Ala Val Gly Gln Val Ser
            980                 985                 990

Ser Phe Ala Pro Asp Tyr Ala Lys Ala Lys Ile Ser Ala Ala His Ile
    995                 1000                1005

Ile Met Ile Ile Glu Lys Thr Pro Leu Ile Asp Ser Tyr Ser Thr Glu
    1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
    1075                1080                1085

Pro Leu Ala Gly Lys Val Leu Leu Asp Gly Lys Glu Ile Lys Arg Leu
    1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
            1125                1130                1135

Ser Arg Val Val Ser Gln Glu Glu Ile Val Arg Ala Ala Lys Glu Ala
```

-continued

```
                    1140                1145                1150
Asn Ile His Ala Phe Ile Glu Ser Leu Pro Asn Lys Tyr Ser Thr Lys
            1155                1160                1165

Val Gly Asp Lys Gly Thr Gln Leu Ser Gly Gln Lys Gln Arg Ile
        1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
            1205                1210                1215

Ala Leu Asp Lys Ala Arg Glu Gly Arg Thr Cys Ile Val Ile Ala His
        1220                1225                1230

Arg Leu Ser Thr Ile Gln Asn Ala Asp Leu Ile Val Val Phe Gln Asn
        1235                1240                1245

Gly Arg Val Lys Glu His Gly Thr His Gln Gln Leu Leu Ala Gln Lys
        1250                1255                1260

Gly Ile Tyr Phe Ser Met Val Ser Val Gln Ala Gly Thr Lys Arg Gln
1265                1270                1275                1280
```

<210> SEQ ID NO 3
<211> LENGTH: 1280
<212> TYPE: PRT
<213> ORGANISM: Homo sapiens

<400> SEQUENCE: 3

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
            85                  90                  95

Asp Ile Asn Asp Thr Gly Phe Phe Met Asn Leu Glu Glu Asp Met Thr
        100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
        130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Val Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
        210                 215                 220

Leu Gly Leu Ser Ala Ala Val Trp Ala Lys Ile Leu Ser Ser Phe Thr
225                 230                 235                 240
```

-continued

```
Asp Lys Glu Leu Leu Ala Tyr Ala Lys Ala Gly Ala Val Ala Glu Glu
            245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
            435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
    515                 520                 525

Ala Gln Leu Ser Gly Gly Gln Lys Gln Arg Ile Ala Ile Ala Arg Ala
530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
            610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
```

-continued

```
            660                 665                 670
Arg Gly Ser Gln Ala Gln Asp Arg Lys Leu Ser Thr Lys Glu Ala Leu
            675                 680                 685
Asp Glu Ser Ile Pro Pro Val Ser Phe Trp Arg Ile Met Lys Leu Asn
            690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Phe Ser Lys Ile Ile
                    725                 730                 735
Gly Val Phe Thr Arg Ile Asp Asp Pro Glu Thr Lys Arg Gln Asn Ser
                    740                 745                 750
Asn Leu Phe Ser Leu Leu Phe Leu Ala Leu Gly Ile Ile Ser Phe Ile
                    755                 760                 765
Thr Phe Phe Leu Gln Gly Phe Thr Phe Gly Lys Ala Gly Glu Ile Leu
                    770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                    805                 810                 815
Arg Leu Ala Asn Asp Ala Ala Gln Val Lys Gly Ala Ile Gly Ser Arg
                    820                 825                 830
Leu Ala Val Ile Thr Gln Asn Ile Ala Asn Leu Gly Thr Gly Ile Ile
                    835                 840                 845
Ile Ser Phe Ile Tyr Gly Trp Gln Leu Thr Leu Leu Leu Ala Ile
                    850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ala Gly Lys Ile
                    885                 890                 895
Ala Thr Glu Ala Ile Glu Asn Phe Arg Thr Val Val Ser Leu Thr Gln
                    900                 905                 910
Glu Gln Lys Phe Glu His Met Tyr Ala Gln Ser Leu Gln Val Pro Tyr
                    915                 920                 925
Arg Asn Ser Leu Arg Lys Ala His Ile Phe Gly Ile Thr Phe Ser Phe
                    930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                    965                 970                 975
Val Phe Ser Ala Val Val Phe Gly Ala Met Ala Val Gly Gln Val Ser
                    980                 985                 990
Ser Phe Ala Pro Asp Tyr Ala Lys Ala Lys Ile Ser Ala Ala His Ile
                    995                 1000                1005
Ile Met Ile Ile Glu Lys Thr Pro Leu Ile Asp Ser Tyr Ser Thr Glu
            1010                1015                1020
Gly Leu Met Pro Asn Thr Leu Glu Gly Asn Val Thr Phe Gly Glu Val
1025                1030                1035                1040
Val Phe Asn Tyr Pro Thr Arg Pro Asp Ile Pro Val Leu Gln Gly Leu
                    1045                1050                1055
Ser Leu Glu Val Lys Lys Gly Gln Thr Leu Ala Leu Val Gly Ser Ser
                    1060                1065                1070
Gly Cys Gly Lys Ser Thr Val Val Gln Leu Leu Glu Arg Phe Tyr Asp
                    1075                1080                1085
```

-continued

Pro Leu Ala Gly Lys Val Leu Leu Asp Gly Lys Glu Ile Lys Arg Leu
    1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
            1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
            1155                1160                1165

Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
            1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
            1235                1240                1245

Gly Arg Val Lys Glu His Gly Thr His Gln Gln Leu Leu Ala Gln Lys
            1250                1255                1260

Gly Ile Tyr Phe Ser Met Val Ser Val Gln Ala Gly Thr Lys Arg Gln
1265                1270                1275                1280

<210> SEQ ID NO 4
<211> LENGTH: 1280
<212> TYPE: PRT
<213> ORGANISM: Homo sapiens

<400> SEQUENCE: 4

Met Asp Leu Glu Gly Asp Arg Asn Gly Gly Ala Lys Lys Lys Asn Phe
1               5                   10                  15

Phe Lys Leu Asn Asn Lys Ser Glu Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Asn Gly Asp Lys Ile Gly Met

-continued

```
                180                 185                 190
Phe Phe Gln Ser Met Ala Thr Phe Thr Gly Phe Ile Val Gly Phe
            195                 200                 205
Thr Arg Gly Trp Lys Leu Thr Leu Val Ile Leu Ala Ile Ser Pro Val
    210                 215                 220
Leu Gly Leu Ser Ala Ala Val Trp Ala Lys Ile Leu Ser Ser Phe Thr
225                 230                 235                 240
Asp Lys Glu Leu Leu Ala Tyr Ala Lys Ala Gly Ala Val Ala Glu Glu
                245                 250                 255
Val Leu Ala Ala Ile Arg Thr Val Ile Ala Phe Gly Gly Gln Lys Lys
            260                 265                 270
Glu Leu Glu Arg Tyr Asn Lys Asn Leu Glu Glu Ala Lys Arg Ile Gly
        275                 280                 285
Ile Lys Lys Ala Ile Thr Ala Asn Ile Ser Ile Gly Ala Ala Phe Leu
    290                 295                 300
Leu Ile Tyr Ala Ser Tyr Ala Leu Ala Phe Trp Tyr Gly Thr Thr Leu
305                 310                 315                 320
Val Leu Ser Gly Glu Tyr Ser Ile Gly Gln Val Leu Thr Val Phe Phe
                325                 330                 335
Ser Val Leu Ile Gly Ala Phe Ser Val Gly Gln Ala Ser Pro Ser Ile
            340                 345                 350
Glu Ala Phe Ala Asn Ala Arg Gly Ala Ala Tyr Glu Ile Phe Lys Ile
        355                 360                 365
Ile Asp Asn Lys Pro Ser Ile Asp Ser Tyr Ser Lys Ser Gly His Lys
    370                 375                 380
Pro Asp Asn Ile Lys Gly Asn Leu Glu Phe Arg Asn Val His Phe Ser
385                 390                 395                 400
Tyr Pro Ser Arg Lys Glu Val Lys Ile Leu Lys Gly Leu Asn Leu Lys
                405                 410                 415
Val Gln Ser Gly Gln Thr Val Ala Leu Val Gly Asn Ser Gly Cys Gly
            420                 425                 430
Lys Ser Thr Thr Val Gln Leu Met Gln Arg Leu Tyr Asp Pro Thr Glu
        435                 440                 445
Gly Met Val Ser Val Asp Gly Gln Asp Ile Arg Thr Ile Asn Val Arg
    450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                485                 490                 495
Met Asp Glu Ile Glu Lys Ala Val Lys Glu Ala Asn Ala Tyr Asp Phe
            500                 505                 510
Ile Met Lys Leu Pro His Lys Phe Asp Thr Leu Val Gly Glu Arg Gly
        515                 520                 525
Ala Gln Leu Ser Gly Gly Gln Lys Gln Arg Ile Ala Ile Ala Arg Ala
    530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
            580                 585                 590
Arg Asn Ala Asp Val Ile Ala Gly Phe Asp Asp Gly Val Ile Val Glu
        595                 600                 605
```

-continued

```
Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
                675                 680                 685

Asp Glu Ser Ile Pro Pro Val Ser Phe Trp Arg Ile Met Lys Leu Asn
690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
                755                 760                 765

Thr Phe Phe Leu Gln Gly Phe Thr Phe Gly Lys Ala Gly Glu Ile Leu
770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
                835                 840                 845

Ile Ser Phe Ile Tyr Gly Trp Gln Leu Thr Leu Leu Leu Leu Ala Ile
850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
                915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys Ala Lys Ile Ser Ala Ala His Ile
                995                 1000                1005

Ile Met Ile Ile Glu Lys Thr Pro Leu Ile Asp Ser Tyr Ser Thr Glu
1010                1015                1020
```

-continued

```
Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
        1075                1080                1085

Pro Leu Ala Gly Lys Val Leu Leu Asp Gly Lys Glu Ile Lys Arg Leu
    1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
        1155                1160                1165

Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
        1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                1270                1275                1280
```

<210> SEQ ID NO 5
<211> LENGTH: 1280
<212> TYPE: PRT
<213> ORGANISM: Homo sapiens

<400> SEQUENCE: 5

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Phe Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125
```

```
Ala Tyr Ile Gln Val Ser Phe Trp Cys Leu Ala Ala Gly Arg Gln Ile
        130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                    165                 170                 175

Asp Asp Val Ser Lys Ile Asn Glu Gly Ile Gly Asp Lys Ile Gly Met
                180                 185                 190

Phe Phe Gln Ser Met Ala Thr Phe Phe Thr Gly Phe Ile Val Gly Phe
            195                 200                 205

Thr Arg Gly Trp Lys Leu Thr Leu Val Ile Leu Ala Ile Ser Pro Val
210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
                275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
515                 520                 525

Ala Gln Leu Ser Gly Gly Gln Lys Gln Arg Ile Ala Ile Ala Arg Ala
530                 535                 540
```

```
Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
```

```
                         965                 970                 975
Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
            995                1000                1005

Ile Met Ile Ile Glu Lys Thr Pro Leu Ile Asp Ser Tyr Ser Thr Glu
   1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
            1045                1050                1055

Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
            1075                1080                1085

Pro Leu Ala Gly Lys Val Leu Leu Asp Gly Lys Glu Ile Lys Arg Leu
            1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
            1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
            1155                1160                1165

Val Gly Asp Lys Gly Thr Gln Leu Ser Gly Gly Gln Lys Gln Arg Ile
   1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
            1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
            1235                1240                1245

Gly Arg Val Lys Glu His Gly Thr His Gln Gln Leu Leu Ala Gln Lys
            1250                1255                1260

Gly Ile Tyr Phe Ser Met Val Ser Val Gln Ala Gly Thr Lys Arg Gln
1265                1270                1275                1280

<210> SEQ ID NO 6
<211> LENGTH: 1280
<212> TYPE: PRT
<213> ORGANISM: Homo sapiens

<400> SEQUENCE: 6

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile His Gly Ala Gly
    50                  55                  60
```

-continued

```
Leu Pro Leu Met Met Leu Val Phe Gly Glu Met Thr Asp Ile Phe Ala
 65              70                  75                  80

Asn Ala Gly Asn Leu Glu Asp Leu Met Ser Asn Ile Thr Asn Arg Ser
             85                  90                  95

Asp Ile Asn Asp Thr Gly Phe Phe Met Asn Leu Glu Glu Asp Met Thr
        100                 105                 110

Arg Tyr Ala Tyr Tyr Tyr Ser Gly Ile Gly Ala Gly Val Leu Val Ala
    115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Phe Gly Met
            180                 185                 190

Phe Phe Gln Ser Phe Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
            245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
    275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
```

-continued

```
                    485                 490                 495
Met Asp Glu Ile Glu Lys Ala Val Lys Glu Ala Asn Ala Tyr Asp Phe
                500                 505                 510
Ile Met Lys Leu Pro His Lys Phe Asp Thr Leu Val Gly Glu Arg Gly
                515                 520                 525
Ala Gln Leu Ser Gly Gln Lys Gln Arg Ile Ala Ile Ala Arg Ala
            530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
                580                 585                 590
Arg Asn Ala Asp Val Ile Ala Gly Phe Asp Asp Gly Val Ile Val Glu
                595                 600                 605
Lys Gly Asn His Asp Glu Leu Met Lys Glu Lys Gly Ile Tyr Phe Lys
            610                 615                 620
Leu Val Thr Met Gln Thr Ala Gly Asn Glu Val Glu Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Arg Ser Val
                660                 665                 670
Arg Gly Ser Gln Ala Gln Asp Arg Lys Leu Ser Thr Lys Glu Ala Leu
            675                 680                 685
Asp Glu Ser Ile Pro Pro Val Ser Phe Trp Arg Ile Met Lys Leu Asn
            690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
                740                 745                 750
Asn Leu Phe Ser Leu Leu Phe Leu Ala Leu Gly Ile Ile Ser Phe Ile
            755                 760                 765
Thr Phe Phe Leu Gln Gly Phe Thr Phe Gly Lys Ala Gly Glu Ile Leu
            770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
            820                 825                 830
Leu Ala Val Ile Thr Gln Asn Ile Ala Asn Leu Gly Thr Gly Ile Ile
            835                 840                 845
Ile Ser Phe Ile Tyr Gly Trp Gln Leu Thr Leu Leu Leu Leu Ala Ile
            850                 855                 860
Val Pro Ile Ile Ala Ile Ala Gly Val Val Glu Met Lys Met Leu Ser
865                 870                 875                 880
Gly Gln Ala Leu Lys Asp Lys Glu Leu Glu Gly Ala Gly Lys Ile
                885                 890                 895
Ala Thr Glu Ala Ile Glu Asn Phe Arg Thr Val Val Ser Leu Thr Gln
                900                 905                 910
```

```
Glu Gln Lys Phe Glu His Met Tyr Ala Gln Ser Leu Gln Val Pro Tyr
    915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Phe Gly Ala Met Ala Val Gly Gln Val Ser
                980                 985                 990

Ser Phe Ala Pro Asp Tyr Ala Lys Ala Lys Ile Ser Ala Ala His Ile
                995                1000                1005

Ile Met Ile Ile Glu Lys Thr Pro Leu Ile Asp Ser Tyr Ser Thr Glu
                1010                1015                1020

Gly Leu Met Pro Asn Thr Leu Glu Gly Asn Val Thr Phe Gly Glu Val
1025                 1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
                1075                1080                1085

Pro Leu Ala Gly Lys Val Leu Leu Asp Gly Lys Glu Ile Lys Arg Leu
                1090                1095                1100

Asn Val Gln Trp Leu Arg Ala His Leu Gly Ile Val Ser Gln Glu Pro
1105                 1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
                1140                1145                1150

Asn Ile His Ala Phe Ile Glu Ser Leu Pro Asn Lys Tyr Ser Thr Lys
                1155                1160                1165

Val Gly Asp Lys Gly Thr Gln Leu Ser Gly Gly Gln Lys Gln Arg Ile
                1170                1175                1180

Ala Ile Ala Arg Ala Leu Val Arg Gln Pro His Ile Leu Leu Leu Asp
1185                 1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
                1220                1225                1230

Arg Leu Ser Thr Ile Gln Asn Ala Asp Leu Ile Val Val Phe Gln Asn
                1235                1240                1245

Gly Arg Val Lys Glu His Gly Thr His Gln Gln Leu Leu Ala Gln Lys
                1250                1255                1260

Gly Ile Tyr Phe Ser Met Val Ser Val Gln Ala Gly Thr Lys Arg Gln
1265                 1270                1275                1280

<210> SEQ ID NO 7
<211> LENGTH: 1280
<212> TYPE: PRT
<213> ORGANISM: Homo sapiens

<400> SEQUENCE: 7

Met Asp Leu Glu Gly Asp Arg Asn Gly Gly Ala Lys Lys Lys Asn Phe
```

```
                1               5                       10                      15
        Phe Lys Leu Asn Asn Lys Ser Glu Lys Asp Lys Lys Glu Lys Lys Pro
                        20                      25                      30
        Thr Val Ser Val Phe Ser Met Phe Arg Tyr Ser Asn Trp Leu Asp Lys
                        35                      40                      45
        Leu Tyr Met Val Val Gly Thr Leu Ala Ala Ile Ile His Gly Ala Gly
                        50                      55                      60
        Leu Pro Leu Met Met Leu Val Phe Gly Glu Met Thr Asp Ile Phe Ala
        65                      70                      75                      80
        Asn Ala Gly Asn Leu Glu Asp Leu Met Ser Asn Ile Thr Asn Arg Ser
                        85                      90                      95
        Asp Ile Asn Asp Thr Gly Phe Phe Met Asn Leu Glu Glu Asp Met Thr
                        100                     105                     110
        Arg Tyr Ala Tyr Tyr Ser Gly Ile Gly Ala Gly Val Leu Val Ala
                        115                     120                     125
        Ala Tyr Ile Gln Val Ser Phe Trp Cys Leu Ala Ala Gly Arg Gln Ile
                        130                     135                     140
        His Lys Ile Arg Lys Gln Phe His Ala Ile Met Arg Gln Glu Ile
        145                     150                     155                     160
        Gly Trp Phe Asp Val His Asp Val Gly Glu Leu Asn Thr Arg Leu Thr
                        165                     170                     175
        Asp Asp Val Ser Lys Ile Asn Glu Gly Ile Gly Asp Lys Ile Gly Met
                        180                     185                     190
        Phe Phe Gln Ser Met Ala Thr Phe Phe Thr Gly Phe Ile Val Gly Phe
                        195                     200                     205
        Thr Arg Gly Trp Lys Leu Thr Leu Val Ile Leu Ala Ile Ser Pro Val
                        210                     215                     220
        Leu Gly Leu Ser Ala Ala Val Trp Ala Lys Ile Leu Ser Ser Phe Thr
        225                     230                     235                     240
        Asp Lys Glu Leu Leu Ala Tyr Ala Lys Ala Gly Ala Val Ala Glu Glu
                        245                     250                     255
        Val Leu Ala Ala Ile Arg Thr Val Ile Ala Phe Gly Gly Gln Lys Lys
                        260                     265                     270
        Glu Leu Glu Arg Tyr Asn Lys Asn Leu Glu Glu Ala Lys Arg Ile Gly
                        275                     280                     285
        Ile Lys Lys Ala Ile Thr Ala Asn Ile Ser Ile Gly Ala Ala Phe Leu
                        290                     295                     300
        Leu Ile Tyr Ala Ser Tyr Ala Leu Ala Phe Trp Tyr Gly Thr Thr Leu
        305                     310                     315                     320
        Val Leu Ser Gly Glu Tyr Ser Ile Gly Gln Val Leu Thr Val Phe Phe
                        325                     330                     335
        Ser Val Leu Ile Gly Ala Phe Ser Val Gly Gln Ala Ser Pro Ser Ile
                        340                     345                     350
        Glu Ala Phe Ala Asn Ala Arg Gly Ala Ala Tyr Glu Ile Phe Lys Ile
                        355                     360                     365
        Ile Asp Asn Lys Pro Ser Ile Asp Ser Tyr Ser Lys Ser Gly His Lys
                        370                     375                     380
        Pro Asp Asn Ile Lys Gly Asn Leu Glu Phe Arg Asn Val His Phe Ser
        385                     390                     395                     400
        Tyr Pro Ser Arg Lys Glu Val Lys Ile Leu Lys Gly Leu Asn Leu Lys
                        405                     410                     415
        Val Gln Ser Gly Gln Thr Val Ala Leu Val Gly Asn Ser Gly Cys Gly
                        420                     425                     430
```

-continued

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Trp Ile Ser Phe Ile
        755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

-continued

Ile Ser Phe Ile Tyr Gly Trp Gln Leu Thr Leu Leu Leu Ala Ile
850                 855                 860

Val Pro Ile Ile Ala Ile Ala Gly Val Val Glu Met Lys Met Leu Ser
865                 870                 875                 880

Gly Gln Ala Leu Lys Asp Lys Glu Leu Glu Gly Ala Gly Lys Ile
            885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
            965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
            995                 1000                1005

Ile Met Ile Ile Glu Lys Thr Pro Leu Ile Asp Ser Tyr Ser Thr Glu
1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
            1045                1050                1055

Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
            1075                1080                1085

Pro Leu Ala Gly Lys Val Leu Leu Asp Gly Lys Glu Ile Lys Arg Leu
            1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
            1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
            1155                1160                1165

Val Gly Asp Lys Gly Thr Gln Leu Ser Gly Gly Gln Lys Gln Arg Ile
1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
            1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
            1235                1240                1245

Gly Arg Val Lys Glu His Gly Thr His Gln Gln Leu Leu Ala Gln Lys
            1250                1255                1260

Gly Ile Tyr Phe Ser Met Val Ser Val Gln Ala Gly Thr Lys Arg Gln

-continued

```
         1265                1270                1275                1280

<210> SEQ ID NO 8
<211> LENGTH: 1280
<212> TYPE: PRT
<213> ORGANISM: Homo sapiens

<400> SEQUENCE: 8

Met Asp Leu Glu Gly Asp Arg Asn Gly Gly Ala Lys Lys Lys Asn Phe
 1               5                  10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365
```

```
Ile Asp Asn Lys Pro Ser Ile Asp Ser Tyr Ser Lys Ser Gly His Lys
370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
                515                 520                 525

Ala Gln Leu Ser Gly Gly Gln Lys Gln Arg Ile Ala Ile Ala Arg Ala
530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
                595                 600                 605

Lys Gly Asn His Asp Glu Leu Met Lys Glu Lys Gly Ile Tyr Phe Lys
610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
                675                 680                 685

Asp Glu Ser Ile Pro Pro Val Ser Phe Trp Arg Ile Met Lys Leu Asn
                690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
                755                 760                 765

Thr Phe Phe Leu Gln Gly Phe Thr Phe Gly Lys Ala Gly Glu Ile Leu
770                 775                 780

Thr Lys Arg Leu Arg Tyr Met Val Phe Arg Ser Met Leu Arg Gln Asp
```

-continued

```
            785                 790                 795                 800
Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Glu Thr Gly Ile Ile
            835                 840                 845

Ile Ser Phe Ile Tyr Gly Trp Gln Leu Thr Leu Leu Leu Ala Ile
        850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
        930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Phe Gly Ala Met Ala Val Gly Gln Val Ser
            980                 985                 990

Ser Phe Ala Pro Asp Tyr Ala Lys Ala Lys Ile Ser Ala Ala His Ile
            995                1000                1005

Ile Met Ile Ile Glu Lys Thr Pro Leu Ile Asp Ser Tyr Ser Thr Glu
        1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
        1075                1080                1085

Pro Leu Ala Gly Lys Val Leu Leu Asp Gly Lys Glu Ile Lys Arg Leu
        1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
            1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
        1155                1160                1165

Val Gly Asp Lys Gly Thr Gln Leu Ser Gly Gln Lys Gln Arg Ile
        1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215
```

```
Ala Leu Asp Lys Ala Arg Glu Gly Arg Thr Cys Ile Val Ile Ala His
        1220                1225                1230

Arg Leu Ser Thr Ile Gln Asn Ala Asp Leu Ile Val Val Phe Gln Asn
        1235                1240                1245

Gly Arg Val Lys Glu His Gly Thr His Gln Leu Leu Ala Gln Lys
        1250                1255                1260

Gly Ile Tyr Phe Ser Met Val Ser Val Gln Ala Gly Thr Lys Arg Gln
1265                1270                1275                1280

<210> SEQ ID NO 9
<211> LENGTH: 1280
<212> TYPE: PRT
<213> ORGANISM: Homo sapiens

<400> SEQUENCE: 9

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
        35                  40                  45

Leu Tyr Met Val Gly Thr Leu Ala Ala Ile His Gly Ala Gly
50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Thr Gly Phe Ile Val Gly Phe
        195                 200                 205

Thr Arg Gly Trp Lys Leu Thr Leu Val Ile Leu Ala Ile Ser Pro Val
        210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
```

-continued

```
305                 310                 315                 320
Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
                515                 520                 525

Ala Gln Leu Ser Gly Gly Gln Lys Gln Arg Ile Ala Ile Ala Arg Ala
                530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
                595                 600                 605

Lys Gly Asn His Asp Glu Leu Met Lys Glu Lys Gly Ile Tyr Phe Lys
                610                 615                 620

Leu Val Thr Met Gln Thr Ala Gly Asn Lys Val Lys Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
                675                 680                 685

Asp Glu Ser Ile Pro Pro Val Ser Phe Trp Arg Ile Met Lys Leu Asn
                690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735
```

```
Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
                755                 760                 765

Thr Phe Phe Leu Gln Gly Phe Thr Phe Gly Lys Ala Gly Glu Ile Leu
                770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
                835                 840                 845

Ile Ser Phe Ile Tyr Gly Trp Gln Leu Thr Leu Leu Leu Leu Ala Ile
                850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
                915                 920                 925

Arg Asn Ser Leu Arg Lys Ala His Ile Phe Gly Ile Thr Phe Ser Phe
                930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys Ala Lys Ile Ser Ala Ala His Ile
                995                 1000                1005

Ile Met Ile Ile Glu Lys Thr Pro Leu Ile Asp Ser Tyr Ser Thr Glu
                1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
                1075                1080                1085

Pro Leu Ala Gly Lys Val Leu Leu Asp Gly Lys Glu Ile Lys Arg Leu
                1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
                1140                1145                1150
```

-continued

Asn Ile His Ala Phe Ile Glu Ser Leu Pro Asn Lys Tyr Ser Thr Lys
    1155                1160                1165

Val Gly Asp Lys Gly Thr Gln Leu Ser Gly Gly Gln Lys Gln Arg Ile
1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
            1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
            1235                1240                1245

Gly Arg Val Lys Glu His Gly Thr His Gln Gln Leu Leu Ala Gln Lys
            1250                1255                1260

Gly Ile Tyr Phe Ser Met Val Ser Val Gln Ala Gly Thr Lys Arg Gln
1265                1270                1275                1280

<210> SEQ ID NO 10
<211> LENGTH: 1280
<212> TYPE: PRT
<213> ORGANISM: Homo sapiens

<400> SEQUENCE: 10

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

-continued

```
Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Lys Ser Lys Ser Lys Ile Asp Ala Leu Lys Met Ser Ser Asn
                645                 650                 655

Asp Ser Arg Ser Ser Leu Ile Arg Lys Arg Ser Thr Arg Arg Ser Val
            660                 665                 670
```

-continued

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
        690                 695                 700

Leu Thr Glu Trp Pro Tyr Phe Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
        770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Ala Ile
        850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys Ala Lys Ile Ser Ala Ala His Ile
        995                 1000                1005

Ile Met Ile Ile Glu Lys Thr Pro Leu Ile Asp Ser Tyr Ser Thr Glu
        1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
        1075                1080                1085

Pro Leu Ala Gly Lys Val Leu Leu Asp Gly Lys Glu Ile Lys Arg Leu

-continued

```
                1090                1095                1100
Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
                1140                1145                1150

Asn Ile His Ala Phe Ile Glu Ser Leu Pro Asn Lys Tyr Ser Thr Lys
                1155                1160                1165

Val Gly Asp Lys Gly Thr Gln Leu Ser Gly Gly Gln Lys Gln Arg Ile
                1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
                1220                1225                1230

Arg Leu Ser Thr Ile Gln Asn Ala Asp Leu Ile Val Val Phe Gln Asn
                1235                1240                1245

Gly Arg Val Lys Glu His Gly Thr His Gln Gln Leu Leu Ala Gln Lys
                1250                1255                1260

Gly Ile Tyr Phe Ser Met Val Ser Val Gln Ala Gly Thr Lys Arg Gln
1265                1270                1275                1280
```

<210> SEQ ID NO 11
<211> LENGTH: 1280
<212> TYPE: PRT
<213> ORGANISM: Homo sapiens

<400> SEQUENCE: 11

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
                100                 105                 110

Arg Tyr Ala Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
                180                 185                 190
```

-continued

Phe Phe Gln Ser Met Ala Thr Phe Thr Gly Phe Ile Val Gly Phe
            195                 200                 205

Thr Arg Gly Trp Lys Leu Thr Leu Val Ile Leu Ala Ile Ser Pro Val
        210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
        290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
            325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
        370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
        450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
        530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

-continued

Lys Gly Asn His Asp Glu Leu Met Lys Glu Lys Gly Ile Tyr Phe Lys
610                 615                 620

Leu Val Thr Met Gln Thr Ala Gly Asn Lys Val Lys Leu Glu Asn Ala
625                 630                 635                 640

Ala Asp Lys Ser Lys Ser Lys Ile Asp Ala Leu Lys Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
                675                 680                 685

Asp Glu Ser Ile Pro Pro Val Ser Phe Trp Arg Ile Met Lys Leu Asn
690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
                755                 760                 765

Thr Phe Phe Leu Gln Gly Phe Thr Phe Gly Lys Ala Gly Glu Ile Leu
770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
                835                 840                 845

Ile Ser Phe Ile Tyr Gly Trp Gln Leu Thr Leu Leu Leu Leu Ala Ile
850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
                915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys Ala Lys Ile Ser Ala Ala His Ile
                995                 1000                1005

Ile Met Ile Ile Glu Lys Thr Pro Leu Ile Asp Ser Tyr Ser Thr Glu
1010                1015                1020

Gly Leu Met Pro Asn Thr Leu Glu Gly Asn Val Thr Phe Gly Glu Val

```
              1025                1030                1035                1040
Val Phe Asn Tyr Pro Thr Arg Pro Asp Ile Pro Val Leu Gln Gly Leu
                    1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
            1075                1080                1085

Pro Leu Ala Gly Lys Val Leu Leu Asp Gly Lys Glu Ile Lys Arg Leu
        1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
                    1140                1145                1150

Asn Ile His Ala Phe Ile Glu Ser Leu Pro Asn Lys Tyr Ser Thr Lys
                1155                1160                1165

Val Gly Asp Lys Gly Thr Gln Leu Ser Gly Gly Gln Lys Gln Arg Ile
            1170                1175                1180

Ala Ile Ala Arg Ala Leu Val Arg Gln Pro His Ile Leu Leu Leu Asp
        1185                1190                1195                1200

Glu Ala Thr Ser Ala Leu Asp Thr Glu Ser Glu Lys Val Val Gln Glu
                    1205                1210                1215

Ala Leu Asp Lys Ala Arg Glu Gly Arg Thr Cys Ile Val Ile Ala His
                1220                1225                1230

Arg Leu Ser Thr Ile Gln Asn Ala Asp Leu Ile Val Val Phe Gln Asn
            1235                1240                1245

Gly Arg Val Lys Glu His Gly Thr His Gln Gln Leu Leu Ala Gln Lys
        1250                1255                1260

Gly Ile Tyr Phe Ser Met Val Ser Val Gln Ala Gly Thr Lys Arg Gln
1265                1270                1275                1280

<210> SEQ ID NO 12
<211> LENGTH: 1280
<212> TYPE: PRT
<213> ORGANISM: Homo sapiens

<400> SEQUENCE: 12

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile His Gly Ala Gly
        50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125
```

```
Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                    165                 170                 175

Asp Asp Val Ser Lys Ile Asn Glu Gly Ile Gly Asp Lys Phe Gly Met
                180                 185                 190

Phe Phe Gln Ser Met Ala Thr Phe Thr Gly Phe Ile Val Gly Phe
            195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
            435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
            515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
```

-continued

```
            545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
                580                 585                 590
Arg Asn Ala Asp Val Ile Ala Gly Phe Asp Asp Gly Val Ile Val Glu
                595                 600                 605
Lys Gly Asn His Asp Glu Leu Met Lys Glu Lys Gly Ile Tyr Phe Lys
            610                 615                 620
Leu Val Thr Met Gln Thr Ala Gly Asn Glu Val Glu Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Arg Ser Val
                660                 665                 670
Arg Gly Ser Gln Ala Gln Asp Arg Lys Leu Ser Thr Lys Glu Ala Leu
            675                 680                 685
Asp Glu Ser Ile Pro Pro Val Ser Phe Trp Arg Ile Met Lys Leu Asn
            690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
                740                 745                 750
Asn Leu Phe Ser Leu Leu Phe Leu Ala Leu Gly Ile Ile Ser Phe Ile
            755                 760                 765
Thr Phe Phe Leu Gln Gly Phe Thr Phe Gly Lys Ala Gly Glu Ile Leu
            770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
                820                 825                 830
Leu Ala Val Ile Thr Gln Asn Ile Ala Asn Leu Gly Thr Gly Ile Ile
            835                 840                 845
Ile Ser Phe Ile Tyr Gly Trp Gln Leu Thr Leu Leu Leu Leu Ala Ile
            850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ala Gly Lys Ile
                885                 890                 895
Ala Thr Glu Ala Ile Glu Asn Phe Arg Thr Val Val Ser Leu Thr Gln
                900                 905                 910
Glu Gln Lys Phe Glu His Met Tyr Ala Gln Ser Leu Gln Val Pro Tyr
            915                 920                 925
Arg Asn Ser Leu Arg Lys Ala His Ile Phe Gly Ile Thr Phe Ser Phe
            930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
```

-continued

```
Val Phe Ser Ala Val Val Phe Gly Ala Met Ala Val Gly Gln Val Ser
            980                 985                 990
Ser Phe Ala Pro Asp Tyr Ala Lys Ala Lys Ile Ser Ala Ala His Ile
            995                1000                1005
Ile Met Ile Ile Glu Lys Thr Pro Leu Ile Asp Ser Tyr Ser Thr Glu
           1010                1015                1020
Gly Leu Met Pro Asn Thr Leu Glu Gly Asn Val Thr Phe Gly Glu Val
1025                1030                1035                1040
Val Phe Asn Tyr Pro Thr Arg Pro Asp Ile Pro Val Leu Gln Gly Leu
            1045                1050                1055
Ser Leu Glu Val Lys Lys Gly Gln Thr Leu Ala Leu Val Gly Ser Ser
            1060                1065                1070
Gly Cys Gly Lys Ser Thr Val Val Gln Leu Leu Glu Arg Phe Tyr Asp
            1075                1080                1085
Pro Leu Ala Gly Lys Val Leu Leu Asp Gly Lys Glu Ile Lys Arg Leu
            1090                1095                1100
Asn Val Gln Trp Leu Arg Ala His Leu Gly Ile Val Ser Gln Glu Pro
1105                1110                1115                1120
Ile Leu Phe Asp Cys Ser Ile Ala Glu Asn Ile Ala Tyr Gly Asp Asn
            1125                1130                1135
Ser Arg Val Val Ser Gln Glu Glu Ile Val Arg Ala Ala Lys Glu Ala
            1140                1145                1150
Asn Ile His Ala Phe Ile Glu Ser Leu Pro Asn Lys Tyr Ser Thr Lys
            1155                1160                1165
Val Gly Asp Lys Gly Thr Gln Leu Ser Gly Gly Gln Lys Gln Arg Ile
            1170                1175                1180
Ala Ile Ala Arg Ala Leu Val Arg Gln Pro His Ile Leu Leu Leu Asp
1185                1190                1195                1200
Glu Ala Thr Ser Ala Leu Asp Thr Glu Ser Glu Lys Val Val Gln Glu
            1205                1210                1215
Ala Leu Asp Lys Ala Arg Glu Gly Arg Thr Cys Ile Val Ile Ala His
            1220                1225                1230
Arg Leu Ser Thr Ile Gln Asn Ala Asp Leu Ile Val Val Phe Gln Asn
            1235                1240                1245
Gly Arg Val Lys Glu His Gly Thr His Gln Gln Leu Leu Ala Gln Lys
            1250                1255                1260
Gly Ile Tyr Phe Ser Met Val Ser Val Gln Ala Gly Thr Lys Arg Gln
1265                1270                1275                1280
```

<210> SEQ ID NO 13
<211> LENGTH: 1280
<212> TYPE: PRT
<213> ORGANISM: Homo sapiens

<400> SEQUENCE: 13

```
Met Asp Leu Glu Gly Asp Arg Asn Gly Gly Ala Lys Lys Lys Asn Phe
1               5                  10                  15
Phe Lys Leu Asn Asn Lys Ser Glu Asp Lys Lys Glu Lys Lys Pro
            20                  25                  30
Thr Val Ser Val Phe Ser Met Phe Arg Tyr Ser Asn Trp Leu Asp Lys
            35                  40                  45
Leu Tyr Met Val Val Gly Thr Leu Ala Ala Ile Ile His Gly Ala Gly
            50                  55                  60
Leu Pro Leu Met Met Leu Val Phe Gly Glu Met Thr Asp Ile Phe Ala
```

-continued

```
            65                  70                  75                  80
Asn Ala Gly Asn Leu Glu Asp Leu Met Ser Asn Ile Thr Asn Arg Ser
                85                  90                  95
Asp Ile Asn Asp Thr Gly Phe Phe Met Asn Leu Glu Glu Asp Met Thr
                100                 105                 110
Arg Tyr Ala Tyr Tyr Ser Gly Ile Gly Ala Gly Val Leu Val Ala
                115                 120                 125
Ala Tyr Ile Gln Val Ser Phe Trp Cys Leu Ala Ala Gly Arg Gln Ile
        130                 135                 140
His Lys Ile Arg Lys Gln Phe Phe His Ala Ile Met Arg Gln Glu Ile
145                 150                 155                 160
Gly Trp Phe Asp Val His Asp Val Gly Glu Leu Asn Thr Arg Leu Thr
                    165                 170                 175
Asp Asp Val Ser Lys Ile Asn Glu Gly Ile Gly Asp Lys Ile Gly Met
                180                 185                 190
Phe Phe Gln Ser Phe Ala Thr Phe Phe Thr Gly Phe Ile Val Gly Phe
            195                 200                 205
Thr Arg Gly Trp Lys Leu Thr Leu Val Ile Leu Ala Ile Ser Pro Val
        210                 215                 220
Leu Gly Leu Ser Ala Ala Val Trp Ala Lys Ile Leu Ser Ser Phe Thr
225                 230                 235                 240
Asp Lys Glu Leu Leu Ala Tyr Ala Lys Ala Gly Ala Val Ala Glu Glu
                245                 250                 255
Val Leu Ala Ala Ile Arg Thr Val Ile Ala Phe Gly Gly Gln Lys Lys
                260                 265                 270
Glu Leu Glu Arg Tyr Asn Lys Asn Leu Glu Glu Ala Lys Arg Ile Gly
            275                 280                 285
Ile Lys Lys Ala Ile Thr Ala Asn Ile Ser Ile Gly Ala Ala Phe Leu
        290                 295                 300
Leu Ile Tyr Ala Ser Tyr Ala Leu Ala Phe Trp Tyr Gly Thr Thr Leu
305                 310                 315                 320
Val Leu Ser Gly Glu Tyr Ser Ile Gly Gln Val Leu Thr Val Phe Phe
                325                 330                 335
Ser Val Leu Ile Gly Ala Phe Ser Val Gly Gln Ala Ser Pro Ser Ile
                340                 345                 350
Glu Ala Phe Ala Asn Ala Arg Gly Ala Ala Tyr Glu Ile Phe Lys Ile
            355                 360                 365
Ile Asp Asn Lys Pro Ser Ile Asp Ser Tyr Ser Lys Ser Gly His Lys
        370                 375                 380
Pro Asp Asn Ile Lys Gly Asn Leu Glu Phe Arg Asn Val His Phe Ser
385                 390                 395                 400
Tyr Pro Ser Arg Lys Glu Val Lys Ile Leu Lys Gly Leu Asn Leu Lys
                405                 410                 415
Val Gln Ser Gly Gln Thr Val Ala Leu Val Gly Asn Ser Gly Cys Gly
                420                 425                 430
Lys Ser Thr Thr Val Gln Leu Met Gln Arg Leu Tyr Asp Pro Thr Glu
            435                 440                 445
Gly Met Val Ser Val Asp Gly Gln Asp Ile Arg Thr Ile Asn Val Arg
        450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                485                 490                 495
```

-continued

Met Asp Glu Ile Glu Lys Ala Val Lys Glu Asn Ala Tyr Asp Phe
             500                 505                 510

Ile Met Lys Leu Pro His Lys Phe Asp Thr Leu Val Gly Glu Arg Gly
            515                 520                 525

Ala Gln Leu Ser Gly Gly Lys Gln Arg Ile Ala Ile Ala Arg Ala
        530                 535                 540

Leu Val Arg Asn Pro Lys Ile Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
            610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
            770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
            835                 840                 845

Ile Ser Phe Ile Tyr Gly Trp Gln Leu Thr Leu Leu Leu Leu Ala Ile
            850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
        930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
        995                 1000                1005

Ile Met Ile Ile Glu Lys Thr Pro Leu Ile Asp Ser Tyr Ser Thr Glu
    1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
            1060                1065                1070

Gly Cys Gly Lys Ser Thr Val Val Gln Leu Leu Glu Arg Phe Tyr Asp
        1075                1080                1085

Pro Leu Ala Gly Lys Val Leu Leu Asp Gly Lys Glu Ile Lys Arg Leu
    1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
            1140                1145                1150

Asn Ile His Ala Phe Ile Glu Ser Leu Pro Asn Lys Tyr Ser Thr Lys
        1155                1160                1165

Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
        1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                1270                1275                1280

<210> SEQ ID NO 14
<211> LENGTH: 1280
<212> TYPE: PRT
<213> ORGANISM: Homo sapiens

<400> SEQUENCE: 14

Met Asp Leu Glu Gly Asp Arg Asn Gly Gly Ala Lys Lys Lys Asn Phe
1               5                   10                  15

-continued

```
Phe Lys Leu Asn Asn Lys Ser Glu Lys Asp Lys Lys Glu Lys Lys Pro
             20                  25                  30

Thr Val Ser Val Phe Ser Met Phe Arg Tyr Ser Asn Trp Leu Asp Lys
             35                  40                  45

Leu Tyr Met Val Val Gly Thr Leu Ala Ala Ile Ile His Gly Ala Gly
         50                  55                  60

Leu Pro Leu Met Met Leu Val Phe Gly Glu Met Thr Asp Ile Phe Ala
 65                  70                  75                  80

Asn Ala Gly Asn Leu Glu Asp Leu Met Ser Asn Ile Thr Asn Arg Ser
                 85                  90                  95

Asp Ile Asn Asp Thr Gly Phe Phe Met Asn Leu Glu Glu Asp Met Thr
             100                 105                 110

Arg Tyr Ala Tyr Tyr Ser Gly Ile Gly Ala Gly Val Leu Val Ala
             115                 120                 125

Ala Tyr Ile Gln Val Ser Phe Trp Cys Leu Ala Ala Gly Arg Gln Ile
         130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                 165                 170                 175

Asp Asp Val Ser Lys Ile Asn Glu Gly Ile Gly Asp Lys Ile Gly Met
             180                 185                 190

Phe Phe Gln Ser Met Ala Thr Phe Phe Thr Gly Phe Ile Val Gly Phe
         195                 200                 205

Thr Arg Gly Trp Lys Leu Thr Leu Val Ile Leu Ala Ile Ser Pro Val
     210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                 245                 250                 255

Val Leu Ala Ala Ile Arg Thr Val Ile Ala Phe Gly Gly Gln Lys Lys
             260                 265                 270

Glu Leu Glu Arg Tyr Asn Lys Asn Leu Glu Glu Ala Lys Arg Ile Gly
         275                 280                 285

Ile Lys Lys Ala Ile Thr Ala Asn Ile Ser Ile Gly Ala Ala Phe Leu
     290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                 325                 330                 335

Ser Val Leu Ile Gly Ala Phe Ser Val Gly Gln Ala Ser Pro Ser Ile
             340                 345                 350

Glu Ala Phe Ala Asn Ala Arg Gly Ala Ala Tyr Glu Ile Phe Lys Ile
         355                 360                 365

Ile Asp Asn Lys Pro Ser Ile Asp Ser Tyr Ser Lys Ser Gly His Lys
370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                 405                 410                 415

Val Gln Ser Gly Gln Thr Val Ala Leu Val Gly Asn Ser Gly Cys Gly
             420                 425                 430
```

-continued

```
Lys Ser Thr Thr Val Gln Leu Met Gln Arg Leu Tyr Asp Pro Thr Glu
    435                 440                 445
Gly Met Val Ser Val Asp Gly Gln Asp Ile Arg Thr Ile Asn Val Arg
    450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                485                 490                 495
Met Asp Glu Ile Glu Lys Ala Val Lys Glu Ala Asn Ala Tyr Asp Phe
                500                 505                 510
Ile Met Lys Leu Pro His Lys Phe Asp Thr Leu Val Gly Glu Arg Gly
        515                 520                 525
Ala Gln Leu Ser Gly Gly Gln Lys Gln Arg Ile Ala Ile Ala Arg Ala
    530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
                580                 585                 590
Arg Asn Ala Asp Val Ile Ala Gly Phe Asp Asp Gly Val Ile Val Glu
    595                 600                 605
Lys Gly Asn His Asp Glu Leu Met Lys Glu Lys Gly Ile Tyr Phe Lys
    610                 615                 620
Leu Val Thr Met Gln Thr Ala Gly Asn Lys Val Glu Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Arg Ser Val
                660                 665                 670
Arg Gly Ser Gln Ala Gln Asp Arg Lys Leu Ser Thr Lys Glu Ala Leu
        675                 680                 685
Asp Glu Ser Ile Pro Pro Val Ser Phe Trp Arg Ile Met Lys Leu Asn
    690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
                740                 745                 750
Asn Leu Phe Ser Leu Leu Phe Leu Ala Leu Gly Ile Ile Ser Phe Ile
        755                 760                 765
Thr Phe Phe Leu Gln Gly Phe Thr Phe Gly Lys Ala Gly Glu Ile Leu
    770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
                820                 825                 830
Leu Ala Val Ile Thr Gln Asn Ile Ala Asn Leu Gly Thr Gly Ile Ile
        835                 840                 845
Ile Ser Phe Ile Tyr Gly Trp Gln Leu Thr Leu Leu Leu Leu Ala Ile
```

-continued

```
              850                 855                 860
Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
                915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Phe Gly Ala Met Ala Val Gly Gln Val Ser
                980                 985                 990

Ser Phe Ala Pro Asp Tyr Ala Lys Ala Lys Ile Ser Ala Ala His Ile
                995                 1000                1005

Ile Met Ile Ile Glu Lys Thr Pro Leu Ile Asp Ser Tyr Ser Thr Glu
    1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
    1075                1080                1085

Pro Leu Ala Gly Lys Val Leu Leu Asp Gly Lys Glu Ile Lys Arg Leu
    1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
                1140                1145                1150

Asn Ile His Ala Phe Ile Glu Ser Leu Pro Asn Lys Tyr Ser Thr Lys
                1155                1160                1165

Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
                1220                1225                1230

Arg Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                1270                1275                1280
```

<210> SEQ ID NO 15
<211> LENGTH: 1280
<212> TYPE: PRT
<213> ORGANISM: Homo sapiens

<400> SEQUENCE: 15

```
Met Asp Leu Glu Gly Asp Arg Asn Gly Gly Ala Lys Lys Lys Asn Phe
 1               5                  10                  15

Phe Lys Leu Asn Asn Lys Ser Glu Lys Lys Glu Lys Lys Pro
             20                  25                  30

Thr Val Ser Val Phe Ser Met Phe Arg Tyr Ser Asn Trp Leu Asp Lys
             35                  40                  45

Leu Tyr Met Val Gly Thr Leu Ala Ala Ile Ile His Gly Ala Gly
     50                  55                  60

Leu Pro Leu Met Met Leu Val Phe Gly Glu Met Thr Asp Ile Phe Ala
65                   70                  75                  80

Asn Ala Gly Asn Leu Glu Asp Leu Met Ser Asn Ile Thr Asn Arg Ser
                 85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
```

-continued

```
            370                 375                 380
Pro Asp Asn Ile Lys Gly Asn Leu Glu Phe Arg Asn Val His Phe Ser
385                 390                 395                 400
Tyr Pro Ser Arg Lys Glu Val Lys Ile Leu Lys Gly Leu Asn Leu Lys
                    405                 410                 415
Val Gln Ser Gly Gln Thr Val Ala Leu Val Gly Asn Ser Gly Cys Gly
                420                 425                 430
Lys Ser Thr Thr Val Gln Leu Met Gln Arg Leu Tyr Asp Pro Thr Glu
            435                 440                 445
Gly Met Val Ser Val Asp Gly Gln Asp Ile Arg Thr Ile Asn Val Arg
450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                    485                 490                 495
Met Asp Glu Ile Glu Lys Ala Val Lys Glu Ala Asn Ala Tyr Asp Phe
                500                 505                 510
Ile Met Lys Leu Pro His Lys Phe Asp Thr Leu Val Gly Glu Arg Gly
            515                 520                 525
Ala Gln Leu Ser Gly Gly Gln Lys Gln Arg Ile Ala Ile Ala Arg Ala
530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                    565                 570                 575
Arg Lys Gly Arg Thr Thr Ile Val Ile Ala His Arg Leu Ser Thr Val
                580                 585                 590
Arg Asn Ala Asp Val Ile Ala Gly Phe Asp Asp Gly Val Ile Val Glu
            595                 600                 605
Lys Gly Asn His Asp Glu Leu Met Lys Glu Lys Gly Ile Tyr Phe Lys
610                 615                 620
Leu Val Thr Met Gln Thr Ala Gly Asn Glu Val Lys Leu Glu Asn Ala
625                 630                 635                 640
Ala Asp Glu Ser Lys Ser Glu Ile Asp Ala Leu Glu Met Ser Ser Asn
                    645                 650                 655
Asp Ser Arg Ser Ser Leu Ile Arg Lys Arg Ser Thr Arg Arg Ser Val
                660                 665                 670
Arg Gly Ser Gln Ala Gln Asp Arg Lys Leu Ser Thr Lys Glu Ala Leu
            675                 680                 685
Asp Glu Ser Ile Pro Pro Val Ser Phe Trp Arg Ile Met Lys Leu Asn
690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                    725                 730                 735
Gly Val Phe Thr Arg Ile Asp Asp Pro Glu Thr Lys Arg Gln Asn Ser
                740                 745                 750
Asn Leu Phe Ser Leu Leu Phe Leu Ala Leu Gly Ile Ile Ser Phe Ile
            755                 760                 765
Thr Phe Phe Leu Gln Gly Phe Thr Phe Gly Lys Ala Gly Glu Ile Leu
            770                 775                 780
Thr Lys Arg Leu Arg Tyr Met Val Phe Arg Ser Met Leu Arg Gln Asp
785                 790                 795                 800
```

-continued

```
Val Ser Trp Phe Asp Asp Pro Lys Asn Thr Thr Gly Ala Leu Thr Thr
            805                 810                 815

Arg Leu Ala Asn Asp Ala Ala Gln Val Lys Gly Ala Ile Gly Ser Arg
        820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys Ala Lys Ile Ser Ala Ala His Ile
            995                 1000                1005

Ile Met Ile Ile Glu Lys Thr Pro Leu Ile Asp Ser Tyr Ser Thr Glu
        1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
            1075                1080                1085

Pro Leu Ala Gly Lys Val Leu Leu Asp Gly Lys Glu Ile Lys Arg Leu
        1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
                1140                1145                1150

Asn Ile His Ala Phe Ile Glu Ser Leu Pro Asn Lys Tyr Ser Thr Lys
            1155                1160                1165

Val Gly Asp Lys Gly Thr Gln Leu Ser Gly Gly Gln Lys Gln Arg Ile
        1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215
```

-continued

```
Ala Leu Asp Lys Ala Arg Glu Gly Arg Thr Cys Ile Val Ile Ala His
            1220                1225                1230

Arg Leu Ser Thr Ile Gln Asn Ala Asp Leu Ile Val Val Phe Gln Asn
        1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                1270                1275                1280
```

<210> SEQ ID NO 16
<211> LENGTH: 1280
<212> TYPE: PRT
<213> ORGANISM: Homo sapiens

<400> SEQUENCE: 16

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
            85                  90                  95

Asp Ile Asn Asp Thr Gly Phe Phe Met Asn Leu Glu Glu Asp Met Thr
        100                 105                 110

Arg Tyr Ala Tyr Tyr Tyr Ser Gly Ile Gly Ala Gly Val Leu Val Ala
    115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
            165                 170                 175

Asp Asp Val Ser Lys Ile Asn Glu Gly Ile Gly Asp Lys Ile Gly Met
        180                 185                 190

Phe Phe Gln Ser Met Ala Thr Phe Phe Thr Gly Phe Ile Val Gly Phe
    195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
            245                 250                 255

Val Leu Ala Ala Ile Arg Thr Val Ile Ala Phe Gly Gly Gln Lys Lys
        260                 265                 270

Glu Leu Glu Arg Tyr Asn Lys Asn Leu Glu Glu Ala Lys Arg Ile Gly
    275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320
```

-continued

Val Leu Ser Gly Glu Tyr Ser Ile Gly Gln Val Leu Thr Val Phe Phe
            325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
            435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
    515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
    595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Lys Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
    675                 680                 685

Asp Glu Ser Ile Pro Pro Val Ser Phe Trp Arg Ile Met Lys Leu Asn
690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

-continued

```
Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
                755                 760                 765

Thr Phe Phe Leu Gln Gly Phe Thr Phe Gly Lys Ala Gly Glu Ile Leu
                770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
                835                 840                 845

Ile Ser Phe Ile Tyr Gly Trp Gln Leu Thr Leu Leu Leu Leu Ala Ile
                850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
                900                 905                 910

Glu Gln Lys Phe Glu His Met Tyr Ala Gln Ser Leu Gln Val Pro Tyr
                915                 920                 925

Arg Asn Ser Leu Arg Lys Ala His Ile Phe Gly Ile Thr Phe Ser Phe
                930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
                980                 985                 990

Ser Phe Ala Pro Asp Tyr Ala Lys Ala Lys Ile Ser Ala Ala His Ile
                995                 1000                1005

Ile Met Ile Ile Glu Lys Thr Pro Leu Ile Asp Ser Tyr Ser Thr Glu
                1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
                1045                1050                1055

Ser Leu Glu Val Lys Lys Gly Gln Thr Leu Ala Leu Val Gly Ser Ser
                1060                1065                1070

Gly Cys Gly Lys Ser Thr Val Val Gln Leu Leu Glu Arg Phe Tyr Asp
                1075                1080                1085

Pro Leu Ala Gly Lys Val Leu Leu Asp Gly Lys Glu Ile Lys Arg Leu
                1090                1095                1100

Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
                1125                1130                1135

Ser Arg Val Val Ser Gln Glu Glu Ile Val Arg Ala Ala Lys Glu Ala
                1140                1145                1150

Asn Ile His Ala Phe Ile Glu Ser Leu Pro Asn Lys Tyr Ser Thr Lys
```

-continued

```
                1155                1160                1165
Val Gly Asp Lys Gly Thr Gln Leu Ser Gly Gly Gln Lys Gln Arg Ile
    1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
                1220                1225                1230

Arg Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                1270                1275                1280

<210> SEQ ID NO 17
<211> LENGTH: 1280
<212> TYPE: PRT
<213> ORGANISM: Homo sapiens

<400> SEQUENCE: 17

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255
```

-continued

```
Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Lys Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
```

-continued

```
                675                 680                 685
Asp Glu Ser Ile Pro Val Ser Phe Trp Arg Ile Met Lys Leu Asn
    690                 695                 700
Leu Thr Glu Trp Pro Tyr Phe Val Val Gly Val Phe Cys Ala Ile Ile
705                 710                 715                 720
Asn Gly Gly Leu Gln Pro Ala Phe Ala Ile Ile Phe Ser Lys Ile Ile
                725                 730                 735
Gly Val Phe Thr Arg Ile Asp Asp Pro Glu Thr Lys Arg Gln Asn Ser
                740                 745                 750
Asn Leu Phe Ser Leu Leu Phe Leu Ala Leu Gly Ile Ile Ser Phe Ile
                755                 760                 765
Thr Phe Phe Leu Gln Gly Phe Thr Phe Gly Lys Ala Gly Glu Ile Leu
    770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
                820                 825                 830
Leu Ala Val Ile Thr Gln Asn Ile Ala Asn Leu Gly Thr Gly Ile Ile
                835                 840                 845
Ile Ser Phe Ile Tyr Gly Trp Gln Leu Thr Leu Leu Leu Leu Ala Ile
    850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ala Gly Lys Ile
                885                 890                 895
Ala Thr Glu Ala Ile Glu Asn Phe Arg Thr Val Val Ser Leu Thr Gln
                900                 905                 910
Glu Gln Lys Phe Glu His Met Tyr Ala Gln Ser Leu Gln Val Pro Tyr
                915                 920                 925
Arg Asn Ser Leu Arg Lys Ala His Ile Phe Gly Ile Thr Phe Ser Phe
    930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
Val Phe Ser Ala Val Val Phe Gly Ala Met Ala Val Gly Gln Val Ser
                980                 985                 990
Ser Phe Ala Pro Asp Tyr Ala Lys Ala Lys Ile Ser Ala Ala His Ile
                995                 1000                1005
Ile Met Ile Ile Glu Lys Thr Pro Leu Ile Asp Ser Tyr Ser Thr Glu
    1010                1015                1020
Gly Leu Met Pro Asn Thr Leu Glu Gly Asn Val Thr Phe Gly Glu Val
1025                1030                1035                1040
Val Phe Asn Tyr Pro Thr Arg Pro Asp Ile Pro Val Leu Gln Gly Leu
                1045                1050                1055
Ser Leu Glu Val Lys Lys Gly Gln Thr Leu Ala Leu Val Gly Ser Ser
                1060                1065                1070
Gly Cys Gly Lys Ser Thr Val Val Gln Leu Leu Glu Arg Phe Tyr Asp
                1075                1080                1085
Pro Leu Ala Gly Lys Val Leu Leu Asp Gly Lys Glu Ile Lys Arg Leu
                1090                1095                1100
```

```
Asn Val Gln Trp Leu Arg Ala His Leu Gly Ile Val Ser Gln Glu Pro
1105                1110                1115                1120

Ile Leu Phe Asp Cys Ser Ile Ala Glu Asn Ile Ala Tyr Gly Asp Asn
            1125                1130                1135

Ser Arg Val Val Ser Gln Glu Ile Val Arg Ala Ala Lys Glu Ala
            1140                1145                1150

Asn Ile His Ala Phe Ile Glu Ser Leu Pro Asn Lys Tyr Ser Thr Lys
            1155                1160                1165

Val Gly Asp Lys Gly Thr Gln Leu Ser Gly Gln Lys Gln Arg Ile
1170                1175                1180

Ala Ile Ala Arg Ala Leu Val Arg Gln Pro His Ile Leu Leu Leu Asp
1185                1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
                1220                1225                1230

Arg Leu Ser Thr Ile Gln Asn Ala Asp Leu Ile Val Val Phe Gln Asn
            1235                1240                1245

Gly Arg Val Lys Glu His Gly Thr His Gln Gln Leu Leu Ala Gln Lys
            1250                1255                1260

Gly Ile Tyr Phe Ser Met Val Ser Val Gln Ala Gly Thr Lys Arg Gln
1265                1270                1275                1280

<210> SEQ ID NO 18
<211> LENGTH: 1280
<212> TYPE: PRT
<213> ORGANISM: Homo sapiens

<400> SEQUENCE: 18

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Gly Thr Leu Ala Ala Ile His Gly Ala Gly
50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
                100                 105                 110

Arg Tyr Ala Tyr Tyr Tyr Ser Gly Ile Gly Ala Gly Val Leu Val Ala
            115                 120                 125

Ala Tyr Ile Gln Val Ser Phe Trp Cys Leu Ala Ala Gly Arg Gln Ile
            130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
```

-continued

```
                195                 200                 205
Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
                275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
            370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
                515                 520                 525

Ala Gln Leu Ser Gly Gly Gln Lys Gln Arg Ile Ala Ile Ala Arg Ala
                530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
            610                 615                 620
```

```
Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Lys Met Ser Ser Asn
            645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
            835                 840                 845

Ile Ser Phe Ile Tyr Gly Trp Gln Leu Thr Leu Leu Leu Leu Ala Ile
850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
            885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
            995                 1000                1005

Ile Met Ile Ile Glu Lys Thr Pro Leu Ile Asp Ser Tyr Ser Thr Glu
    1010                1015                1020

Gly Leu Met Pro Asn Thr Leu Glu Gly Asn Val Thr Phe Gly Glu Val
1025                1030                1035                1040
```

```
                                    -continued
Val Phe Asn Tyr Pro Thr Arg Pro Asp Ile Pro Val Leu Gln Gly Leu
                1045            1050            1055

Ser Leu Glu Val Lys Lys Gly Gln Thr Leu Ala Leu Val Gly Ser Ser
                1060            1065            1070

Gly Cys Gly Lys Ser Thr Val Val Gln Leu Leu Glu Arg Phe Tyr Asp
            1075            1080            1085

Pro Leu Ala Gly Lys Val Leu Leu Asp Gly Lys Glu Ile Lys Arg Leu
        1090            1095            1100

Asn Val Gln Trp Leu Arg Ala His Leu Gly Ile Val Ser Gln Glu Pro
1105            1110            1115            1120

Ile Leu Phe Asp Cys Ser Ile Ala Glu Asn Ile Ala Tyr Gly Asp Asn
                1125            1130            1135

Ser Arg Val Val Ser Gln Glu Glu Ile Val Arg Ala Ala Lys Glu Ala
                1140            1145            1150

Asn Ile His Ala Phe Ile Glu Ser Leu Pro Asn Lys Tyr Ser Thr Lys
            1155            1160            1165

Val Gly Asp Lys Gly Thr Gln Leu Ser Gly Gly Gln Lys Gln Arg Ile
        1170            1175            1180

Ala Ile Ala Arg Ala Leu Val Arg Gln Pro His Ile Leu Leu Leu Asp
1185            1190            1195            1200

Glu Ala Thr Ser Ala Leu Asp Thr Glu Ser Glu Lys Val Val Gln Glu
                1205            1210            1215

Ala Leu Asp Lys Ala Arg Glu Gly Arg Thr Cys Ile Val Ile Ala His
                1220            1225            1230

Arg Leu Ser Thr Ile Gln Asn Ala Asp Leu Ile Val Val Phe Gln Asn
            1235            1240            1245

Gly Arg Val Lys Glu His Gly Thr His Gln Gln Leu Leu Ala Gln Lys
        1250            1255            1260

Gly Ile Tyr Phe Ser Met Val Ser Val Gln Ala Gly Thr Lys Arg Gln
1265            1270            1275            1280
```